(12) United States Patent
Levy et al.

(10) Patent No.: US 12,702,469 B2
(45) Date of Patent: Aug. 11, 2026

(54) APPARATUS AND METHOD FOR TRANSSEPTAL PUNCTURE BASED ON IMPEDANCE

(71) Applicant: Biosense Webster (Israel) Ltd., Yokneam (IL)

(72) Inventors: Yitzhak Tzachi Levy, Irvine, CA (US); Vitaliy Putra, Irvine, CA (US); Kruti Shah, Mission Viejo, CA (US); Tonima R. Quabili, Laguna Hills, CA (US); Paul A Suárez, La Crescenta, CA (US); Maria Duarte, Chino, CA (US); Erica E. Lovejoy, La Puente, CA (US); Kokou A. Amefia, Aliso Viejo, CA (US); Debby E. Highsmith, Laguna Niguel, CA (US); Eajer Toh, Sugar Land, TX (US)

(73) Assignee: Biosense Webster (Israel) Ltd., Yokneam (IL)

( * ) Notice: Subject to any disclaimer, the term of this patent is extended or adjusted under 35 U.S.C. 154(b) by 244 days.

(21) Appl. No.: 18/335,932

(22) Filed: Jun. 15, 2023

(65) Prior Publication Data

US 2024/0000497 A1 Jan. 4, 2024

Related U.S. Application Data

(60) Provisional application No. 63/356,684, filed on Jun. 29, 2022.

(51) Int. Cl.
*A61B 18/14* (2006.01)
*A61B 18/00* (2006.01)

(52) U.S. Cl.
CPC .... *A61B 18/14* (2013.01); *A61B 2018/00601* (2013.01); *A61B 2018/00875* (2013.01); *A61B 2018/1425* (2013.01)

(58) Field of Classification Search
CPC .......... A61B 18/14; A61B 2018/00601; A61B 2018/00875; A61B 2018/1425;
(Continued)

(56) References Cited

U.S. PATENT DOCUMENTS

| | | | |
|---|---|---|---|
| 4,532,924 | A | 8/1985 | Auth et al. |
| 4,848,352 | A | 7/1989 | Pohndorf et al. |

(Continued)

FOREIGN PATENT DOCUMENTS

| | | | |
|---|---|---|---|
| EP | 2340778 | B1 | 5/2014 |
| JP | 4511935 | B2 | 7/2010 |

(Continued)

OTHER PUBLICATIONS

European Extended Search Report and Written Opinion dated Nov. 27, 2023, for Application No. 23182120.8, 13 pages.

(Continued)

*Primary Examiner* — Beverly M Flanagan
(74) *Attorney, Agent, or Firm* — FBT Gibbons LLP

(57) ABSTRACT

A transseptal puncture system and method uses a guiding instrument, and an atraumatic puncture instrument longitudinally movable therein, with a first electrode configured for ablation and a second electrode electrically insulated from the first electrode. An impedance monitoring module is configured to measure at least an impedance at the second electrode, and an electrical generator is configured to selectively apply electrical energy to the first electrode based at least in part on the measured impedance at the second electrode. Moreover, impedance measurements at the first and second electrodes are used to determine relative positions of the instruments in the approach, contact, ablation and puncture of the septum.

13 Claims, 16 Drawing Sheets

(58) Field of Classification Search
CPC ........... A61B 2018/00351; A61B 2018/00577; A61B 2017/00026; A61B 2017/00247
USPC ............................................................ 606/41
See application file for complete search history.

(56) References Cited

U.S. PATENT DOCUMENTS

| | | | |
|---|---|---|---|
| 4,998,933 | A | 3/1991 | Eggers et al. |
| 5,419,767 | A | 5/1995 | Eggers et al. |
| 5,836,875 | A | 11/1998 | Webster, Jr. |
| 5,944,022 | A | 8/1999 | Nardella et al. |
| 5,983,126 | A | 11/1999 | Wittkampf |
| 6,241,724 | B1 | 6/2001 | Fleischman et al. |
| 6,456,864 | B1 | 9/2002 | Swanson et al. |
| 6,994,094 | B2 | 2/2006 | Schwartz |
| 7,077,842 | B1 | 7/2006 | Cosman |
| 7,266,414 | B2 | 9/2007 | Cornelius et al. |
| 8,095,212 | B2 | 1/2012 | Sato |
| 8,152,829 | B2 | 4/2012 | Scheib |
| 8,282,633 | B2 | 10/2012 | Sato et al. |
| 8,456,182 | B2 | 6/2013 | Bar-Tal et al. |
| 8,478,383 | B2 | 7/2013 | Bar-Tal et al. |
| 9,693,764 | B2 | 7/2017 | Keidar |
| 9,848,943 | B2 | 12/2017 | Beeckler et al. |
| 10,398,347 | B2 | 9/2019 | Pressman et al. |
| 10,603,472 | B2 | 3/2020 | Gliner et al. |
| 11,213,344 | B2 | 1/2022 | Gliner |
| 11,583,312 | B2 | 2/2023 | Howard et al. |
| 2004/0220461 | A1 | 11/2004 | Schwartz |
| 2004/0220471 | A1 | 11/2004 | Schwartz |
| 2006/0135962 | A1 | 6/2006 | Kick et al. |
| 2007/0016007 | A1 | 1/2007 | Govari et al. |
| 2008/0119846 | A1 | 5/2008 | Rioux |
| 2009/0171187 | A1 | 7/2009 | Gerhart et al. |
| 2013/0281978 | A1 | 10/2013 | Nance et al. |
| 2018/0064359 | A1 | 3/2018 | Pranaitis et al. |
| 2019/0059994 | A1 | 2/2019 | Shin et al. |
| 2019/0307500 | A1 | 10/2019 | Byrd et al. |
| 2020/0129086 | A1 | 4/2020 | Ganapathy et al. |
| 2021/0085384 | A1 | 3/2021 | Maini |
| 2021/0196370 | A1 | 7/2021 | Govari |
| 2021/0401483 | A1 | 12/2021 | Highsmith et al. |
| 2022/0061911 | A1* | 3/2022 | Howard ............. A61B 17/3478 |
| 2022/0110513 | A1 | 4/2022 | Palushi et al. |
| 2022/0110577 | A1 | 4/2022 | Highsmith et al. |
| 2022/0257093 | A1 | 8/2022 | Tarke et al. |
| 2022/0370121 | A1 | 11/2022 | Highsmith |
| 2023/0181241 | A1 | 6/2023 | Suárez et al. |
| 2023/0329771 | A1 | 10/2023 | Davies et al. |
| 2024/0000504 | A1 | 1/2024 | Suarez et al. |

FOREIGN PATENT DOCUMENTS

| | | | | |
|---|---|---|---|---|
| WO | 2013/101632 | A1 | 7/2013 | |
| WO | WO-2018175348 | A1 * | 9/2018 | ........... A61B 5/0538 |
| WO | 2022/090896 | A1 | 5/2022 | |

OTHER PUBLICATIONS

European Extended Search Report and Written Opinion dated Dec. 6, 2023, for Application No. 23182157.0, 7 pages.

* cited by examiner

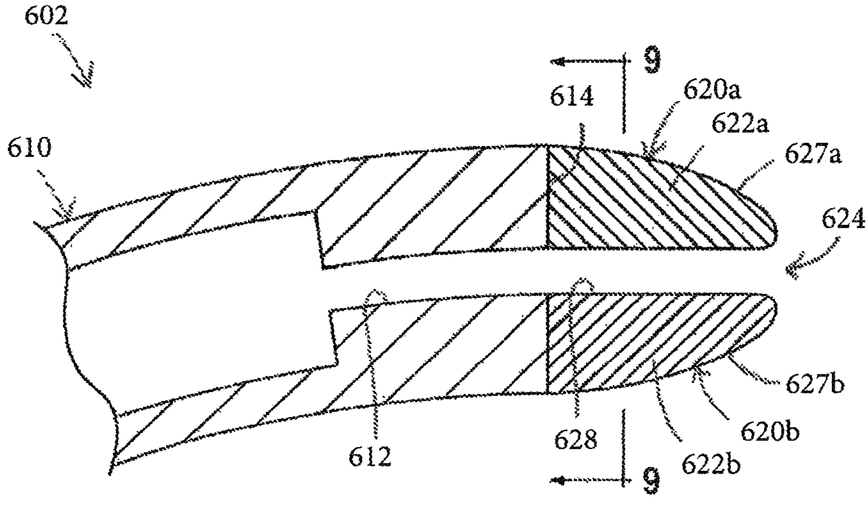
FIG. 8
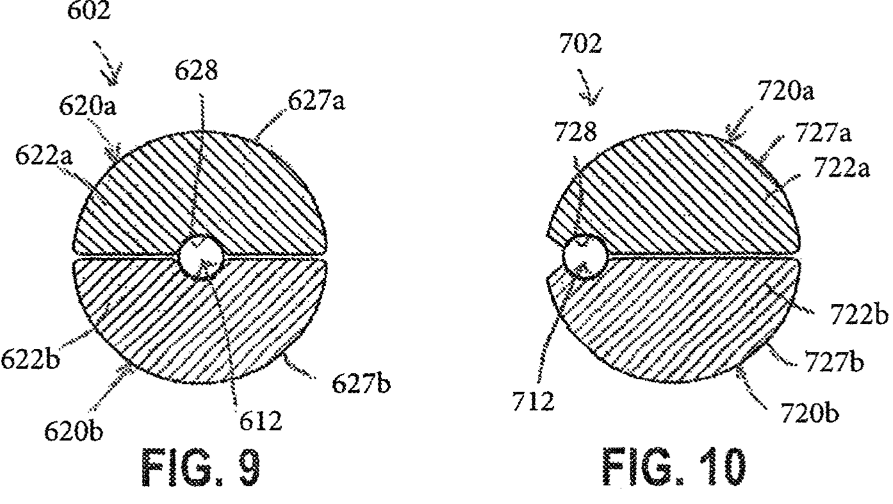
FIG. 9
FIG. 10

802
820a
822a
820b
822b
821a
810
827
821b
828
826

12
827
820b
822b
814
824
822a
826
828
820a
821a
821b
812
802
810

904
940
962a
962b
962a
962b
962a
944
950
954
952

904
940
962a
962b
962a
950
954
962b
962a 962a
904
962a
950
940
954
962b
962b 962a
962b
904
962a
962a
940
962a
950
954
962b

S
1105
1114
1147
1145

1147
S
1105
1114
1145

1145
S
1105
1147

1105
1114
1145
S
1147
1147
1145

1105
1114
S

1105
S
1145

1114
1105
1145
S

1145
S
1105
1147

1114
S
1105
1147
1145

1145
S
1105
1114
1147

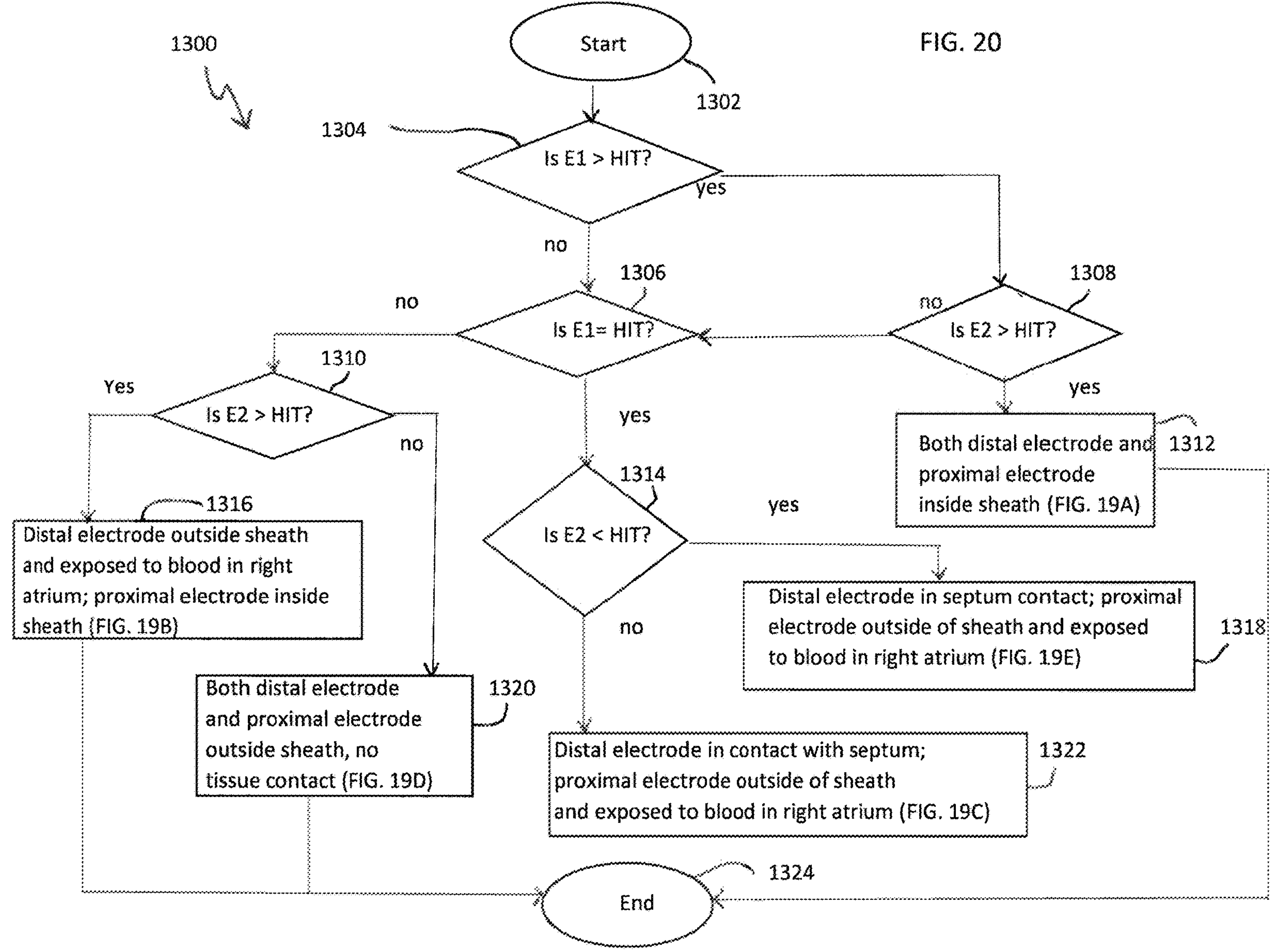
FIG. 20
1300
Start
1302
1304
Is E1 > HIT?
yes
no
1306
Is E1= HIT?
1308
no
Is E2 > HIT?
yes
Both distal electrode and proximal electrode inside sheath (FIG. 19A)
1312
no
1310
Yes
Is E2 > HIT?
no
yes
1314
Is E2 < HIT?
yes
1316
Distal electrode outside sheath and exposed to blood in right atrium; proximal electrode inside sheath (FIG. 19B)
Distal electrode in septum contact; proximal electrode outside of sheath and exposed to blood in right atrium (FIG. 19E)
1318
no
Both distal electrode and proximal electrode outside sheath, no tissue contact (FIG. 19D)
1320
Distal electrode in contact with septum; proximal electrode outside of sheath and exposed to blood in right atrium (FIG. 19C)
1322
1324
End

APPARATUS AND METHOD FOR TRANSSEPTAL PUNCTURE BASED ON IMPEDANCE

CROSS-REFERENCE TO RELATED APPLICATION(S)

This application claims priority to and the benefit of U.S. Provisional Patent Application No. 63/356,684 filed Jun. 29, 2022, the entire content of which is incorporated herein by reference.

FIELD OF THE INVENTION

The present invention is directed toward methods and instruments for performing diagnostic or therapeutic procedures on tissue and organs, in particular, methods and instruments for perforation procedures such as a transseptal perforation procedure.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of electrical energy (e.g., radiofrequency (AC type) or irreversible electroporation (IRE), such as pulsed field (DC type) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with electrical energy to thereby ablate the contacted tissue. In some cases, the electrodes may be bipolar. In some other cases, a monopolar electrode may be used in conjunction with a ground pad or other reference electrode that is in contact with the patient. Irrigation may be used to draw heat from ablating components of an ablation catheter; and to prevent the formation of blood clots near the ablation site.

In some instances, it may be desirable to traverse the atrial septum to facilitate access various types of cardiac interventions in the left atrium of the heart, including electrophysiological or structural testing, treatment (e.g., ablation), or mapping. To achieve traversal of the atrial septum, a needle, guidewire, or other instrument may be used to form an opening through the septum. Examples of transseptal needles and associated components are disclosed in U.S. Pat. No. 6,994,094, entitled "Method and Device for Transseptal Facilitation Based on Injury Patterns," issued Feb. 7, 2006, the disclosure of which is incorporated by reference herein, in its entirety; U.S. Pat. No. 8,152,829, entitled "Retractable Dilator Needle," issued Apr. 10, 2012, the disclosure of which is incorporated by reference herein, in its entirety; U.S. Pat. No. 9,848,943, entitled "Ablation Catheter with Dedicated Fluid Paths and Needle Centering Insert," issued Dec. 26, 2017, the disclosure of which is incorporated by reference herein, in its entirety; U.S. Pub. No 2004/0220471, entitled "Method and Device for Transseptal Facilitation Using Location System," published Nov. 4, 2004, now abandoned, the disclosure of which is incorporated by reference herein, in its entirety; and U.S. Pub. No 2004/0220461, entitled "Transseptal Facilitation Using Sheath with Electrode Arrangement," published Nov. 4, 2004, now abandoned, the disclosure of which is incorporated by reference herein, in its entirety. Some transseptal needle instruments include a dilation feature that further expands the opening formed through the atrial septum.

Tissue puncture using an electrically active guidewire is disclosed in U.S. application Ser. No. 17/743,852, entitled "Tissue Puncture Using High Articulation Microcatheter and Electrically Active Guidewire," filed May 13, 2022, the disclosure of which is incorporated herein by reference, in its entirety. Some transseptal puncturing systems include, for example, a steerable microcatheter, a dilator, a sheath or a guidewire, along with a navigation module and an impedance monitoring module. The system and related method provide for a microcatheter with a location sensor, the guidewire with an electrically conductive ablation distal end, where the navigation module can be configured to determine a position of the distal end of the microcatheter based at least in part on the location sensor in reference to the distal end of the guidewire. The system and related method further provide for (i) measuring an impedance at the electrically-conductive ablation distal end of the guidewire [0018], (ii) determining a position of the ablation distal end of the guidewire based at least in part on the impedance[0025], and (iii) detecting contact of the ablation distal end with tissue based at least in part on the impedance [0026]. Moreover, initiating application of and terminating electrical energy to the ablation distal end of the guidewire can be based at least in part on the impedance.

While transeptal puncture and dilation systems and methods have been made and used, it is believed that no one prior to the inventors has made or used the invention described, illustrated and claimed herein. In particular, Applicants recognize that there is a need for measurement of impedance via an non-ablating electrode less susceptible to microbubble formation and significant "noise" to provide greater resolution of impedance changes, where such impedance measurement can be used to detect if a distal tip of a needle instrument is in within a lumen or outside in contact with blood, and if the distal tip has contacted and crossed through the septum.

SUMMARY OF THE DISCLOSURE

Embodiments of the present invention are directed to transseptal puncture systems and methods that use a guiding instrument, and an atraumatic puncture instrument longitudinally movable therein, with a first electrode configured for ablation and a second electrode electrically insulated from the first electrode. An impedance monitoring module is configured to measure an impedance at at least the second electrode, and an electrical generator is configured to selectively apply electrical energy to the first electrode based at least in part on the measured impedance at the second electrode. Moreover, impedance measurements at both the first and second electrodes are used to determine relative positions of the instruments in the approach, contact, ablation and puncture of the septum.

In some embodiments, a transseptal puncture system include a lumened instrument, a needle instrument, an electrical generator and an impedance monitoring module.

The needle instrument is advanced distally relative to a distal end of the lumened instrument to contact and ablate tissue, including a septum, via an electrically-conductive element or first electrode in puncturing the septum to enter a left atrium. The needle instrument advantageously includes a second electrode configured for impedance measurement, and the system is configured to determine position of the needle instrument based at least in part on a measured impedance at the second electrode.

In some embodiments, the system determines position of the needle instrument at various stages of a transseptal puncture procedure, including approach, contact, penetration, perforation or passage through the septum, based at least in part on the measured impedance at the second electrode.

In some embodiments, the first and second electrodes are separated by a predetermined distance.

In some embodiments, the first and second electrodes are electrically insulated from each other.

In some embodiments, the second electrode is proximal of the first electrode on the needle instrument.

In some embodiments, the second electrode and the first electrodes generally share a common longitudinal location on the needle instrument.

In some embodiments, the second electrode is nonablating.

In some embodiments, the system includes a return pad.

In some embodiments, the first electrode includes a ring electrode.

In some embodiments, the first electrode includes a distal tip electrode.

In some embodiments, the first electrode includes a distal dome electrode.

In some embodiments, a distal end of the needle instrument is atraumatic.

In some embodiments, a distal end of the needle instrument is lacking a piercing configuration.

In some embodiments, the second electrode includes a ring electrode.

In some embodiments, the system includes a navigation module.

In some embodiments, the impedance monitoring module is communication with the electrical generator, in electrical communication with the second electrode and configured to measure impedance at the second electrode. The electrical generator can be configured to provide electrical energy to the first electrode based at least in part on the impedance measured at the proximal electrode by the impedance monitoring module.

In some embodiments, a transseptal puncture method includes steering a lumened instrument that guides a needle instrument advanced therethrough to a target puncture site then puncturing the target puncture site with the needle instrument. The method includes applying electrical energy to an electrically-conductive element or first electrode of the needle instrument for ablating the target puncture site in penetrating tissue and measuring impedance at a second electrode for determining position of the needle instrument in various stages of a transseptal puncture procedure, including approach, contact, penetration or passage through the septum.

In some embodiments, the method includes applying electrical energy to the first electrode based in part on an impedance measured at the second electrode.

In some embodiments, the method includes suspending application of electrical energy to the first electrode based in part on an impedance measured at the second electrode.

In some embodiments, the method includes measuring impedance at the first electrode to determine an increase in impedance.

In some embodiments, the method includes measuring impedance at the first electrode to determine a decrease in impedance.

In some embodiments, the method includes measuring impedance at the second electrode to determine an increase in impedance.

In some embodiments, the method includes measuring impedance at the second electrode to determine a decrease in impedance.

In some embodiments, the method includes measuring impedance at the first electrode and comparing a measured impedance to a predetermined threshold.

In some embodiments, the method includes measuring impedance at the second electrode and comparing a measured impedance to a predetermined threshold, In some embodiments, a transseptal puncture method includes steering a lumened instrument that guides a needle instrument advanced therethrough to a target puncture site then puncturing the target puncture site with the needle instrument via ablation by selectively applying electrical energy to the needle instrument. The needle instrument includes a first electrode configured to ablate tissue and a second electrode electrically insulated from the first electrode. The method includes measuring impedance at the second electrode, including increase and decrease of impedance, and selectively applying electrical energy to the first electrode in response to the increase and the decrease of impedance measured.

In some embodiments, the method includes measuring impedances at the first electrode and the second electrode and comparing measured impedances of the first electrode and of the second electrode and of a predetermined threshold in determining relative position of the needle instrument in various stages of a transseptal puncture procedure, including approach, contact, penetration or passage through the septum from a first atrium to a second atrium.

In some embodiments, the method includes comparing the measured impedance of the first electrode and the measured impedance of the second electrode with each other.

In some embodiments, the method includes comparing the measured impedance of the first electrode and the predetermined threshold to each other.

In some embodiments, the method includes comparing the measured impedance of the second electrode and the predetermined threshold to each other.

In some embodiments, the method includes determining a baseline impedance for an electrode devoid of contact with septum tissue or blood.

In some embodiments, the predetermined threshold is a measured impedance of an electrode in contact with septum tissue.

In some embodiments, a transseptal puncture system includes a guiding instrument configured with a lumen, and an elongated instrument configured to move longitudinally within the lumen, the instrument having a distal end and including a first electrode configured for ablation and a second electrode electrically insulated from the first electrode. The system also includes an impedance monitoring module configured to measure an impedance at the second electrode, and an electrical generator configured to selectively apply electrical energy to the first electrode based at least in part on the measured impedance.

In some embodiments, the guiding instrument includes a guiding sheath.

In some embodiments, the elongated instrument includes a needle instrument.

In some embodiments, the first electrode is distal of the second electrode.

In some embodiments, the first electrode is atraumatic, being devoid of a tissue-piercing distal end.

In some embodiments, the first electrode is configured as a monopolar electrode for tissue ablation.

In some embodiments, the first electrode is configured as a bipolar electrode for tissue ablation.

In some embodiments, the first electrode and the second electrode are separate on the elongated instrument by a predetermined distance.

In some embodiments, the system includes a return pad that is configured to be affixed to a patient's body to enable the impedance monitoring module to measure impedance at the second electrode.

In some embodiments, electrical energy applied to the second electrode generates a current that is distributed through the patient's body to the return pad.

In some embodiments, a method of transseptal puncture includes positioning a guiding instrument near a septum, a needle instrument positioned in a lumen of the guiding instrument, the needle instrument including a first electrode and a second electrode. The method also includes deploying the needle instrument from the lumen with distal advancement relative to the guiding instrument, and measuring an impedance at at least one of the first and second electrodes. The method further includes selectively energizing the first electrode to ablate the septum in creating a puncture in the septum based on the impedance measured.

In some embodiments, the measuring an impedance includes measuring at the second electrode an increase in the impedance measured.

In some embodiments, the measuring an impedance at the second electrode includes measuring a decrease in the impedance measured.

In some embodiments, the measuring an impedance at the second electrode includes measuring an increase in impedance following a decrease in impedance, and the selectively energizing the first electrode includes suspending energization of the first electrode upon measuring the decrease in impedance.

In some embodiments, the method further includes suspending distal advancement of the needle instrument upon measuring an impedance at the second electrode that includes an increase following by a decrease.

In some embodiments, a method of determining position of a needle instrument relative to a guiding sheath and a septum includes the needle instrument to include a first electrode and a second electrode, the first electrode configured to puncture the septum via ablation. The method includes providing a predetermined threshold impedance, determining a first measured impedance of the first electrode, determining a second measured impedance of the second electrode, comparing the first measured impedance with the predetermined threshold impedance, and comparing the second measured impedance with the predetermined threshold impedance.

In some embodiments, the method further includes selectively providing electrical energy to the first electrode for ablation when at least the first measured impedance is equal to the predetermined threshold impedance.

In some embodiments, the method further includes suspending electrical energy to the first electrode when at least the second measure impedance decreases following an increase.

In some embodiments, the method further includes selectively providing electrical energy to the first electrode for ablation when at least the second measured impedance is less than the predetermined threshold impedance.

BRIEF DESCRIPTION OF THE DRAWINGS

The drawings and detailed description that follow are intended to be merely illustrative and are not intended to limit the scope of the invention as contemplated by the inventors.

FIG. 8 depicts a cross-sectional side view of a distal portion of another example of a dilator for use with the transseptal puncture instrument of FIG. 4A and having a pair of adjacent distal tip members surrounding a guidewire lumen of the dilator;

FIG. 9 depicts a cross-sectional end view of the dilator of FIG. 8, taken along line 9-9 of FIG. 8;

FIG. 10 depicts a cross-sectional end view of a distal portion of another example of a dilator for use with the transseptal puncture instrument of FIG. 4A and having a pair of adjacent distal tip members offset from a guidewire lumen of the dilator;

FIG. 20 is a flow diagram outlining steps of an example method for determining position of a needle instrument relative to a sheath and a septum.

DETAILED DESCRIPTION OF THE PREFERRED EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Overview of Example of a Catheter System

Figure 1:
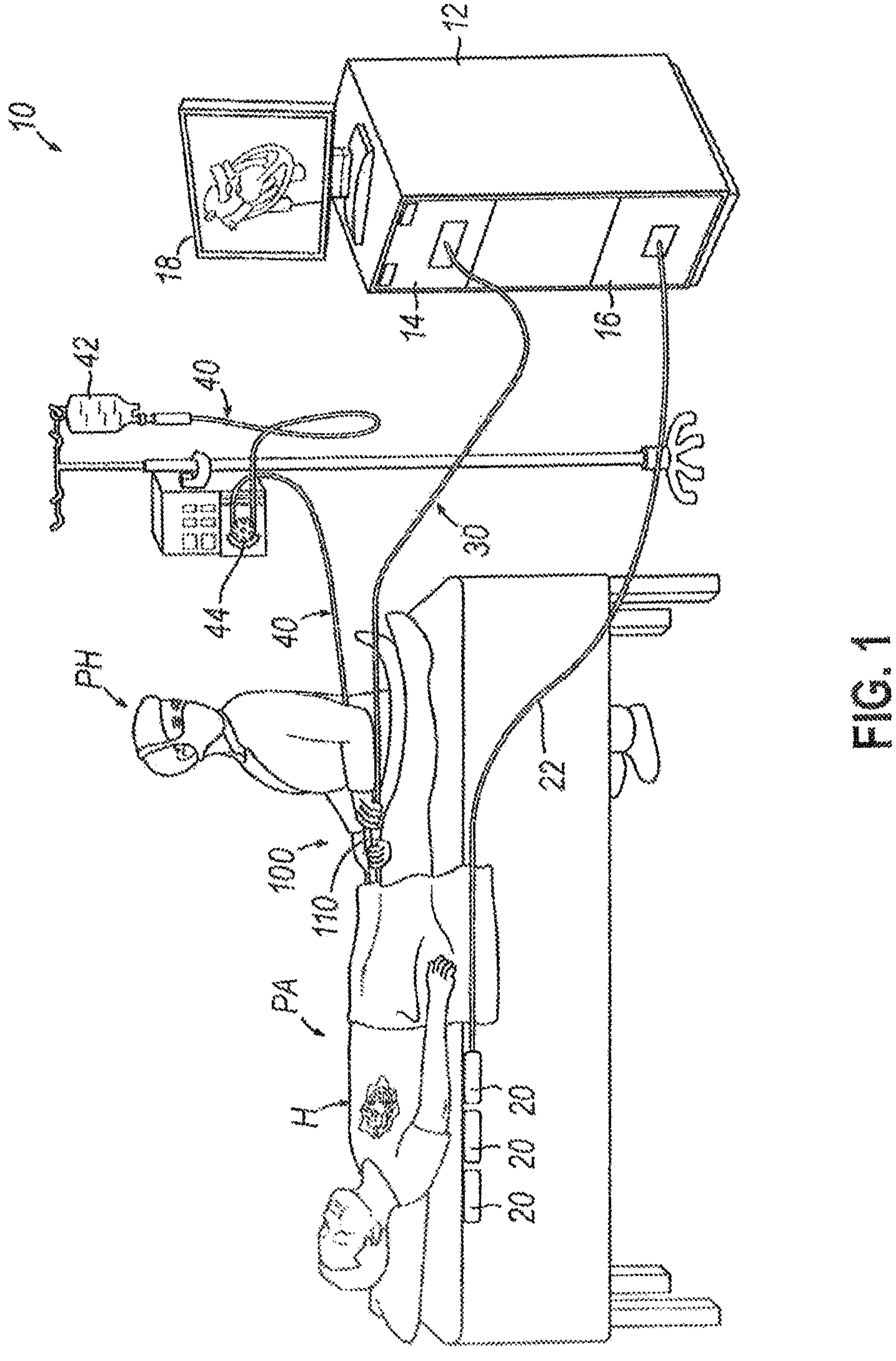
FIG. 1 depicts a schematic view of a medical procedure in which a catheter of a catheter assembly is inserted in a patient.

FIG. 1 shows an exemplary medical procedure and associated components of a cardiac catheter system that may be used to provide EP mapping or cardiac ablation as referred to above. In particular, FIG. 1 shows a physician (PH) grasping a handle assembly (110) of a catheter assembly (100), with an end effector (not shown) of a catheter of catheter assembly (100) disposed in a patient (PA) to map potentials in tissue and/or ablate tissue in or near the heart (H) of the patient (PA). The end effector may include various electrodes, sensors, and/or other features that are configured to deliver electrical energy (e.g., RF or IRE, etc.) to targeted tissue sites, provide EP mapping functionality, track external forces imparted on the end effector, track the location of end effector, and/or disperse fluid. In some instances, the catheter assembly (100) includes a needle instrument, for example, a guidewire, with an electrically-conductive ablation distal end to form an opening in the septum, and a sheath to guide the needle instrument to the septum, where the needle instrument includes an nonablating electrode that is proximal of the ablation distal end and configured to generate impedance signals.

Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Magnetic field generators (20) are merely optional. Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes of the end effector of catheter assembly (100). In some variations, first driver module (14) includes a navigation module that is in connection with catheter assembly location sensor(s) and operable to determine a position of catheter components in the heart based at least in part on the location sensor(s) in reference to the electrically conductive distal end of the needle instrument. Console (12) includes a processor (not shown) that processes such EP mapping signals and thereby provides EP mapping as is known in the art.

First driver module (14) of the present example is further operable to provide electrical energy to a distal tip member of the end effector of catheter assembly (100), to thereby ablate tissue. Second driver module (16) is coupled with magnetic field generators (20) via cable (22). Second driver module (16) is operable to activate magnetic field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a navigation sensor assembly in or near the end effector of catheter assembly (100). In such versions, the processor of console (12) is also operable to process the position indicative signals from the navigation sensor assembly to thereby determine the position of the end effector of catheter assembly (100) within the patient (PA). In some versions, the navigation sensor assembly includes two or more coils that are operable to generate signals that are indicative of the position and orientation of the end effector of catheter assembly (100) within the patient (PA). The coils are configured to generate electrical signals in response to the presence of an alternating electromagnetic field generated by magnetic field generators (20).

In some embodiment, first driver module (14) includes an impedance monitoring module and the processor of console (12) is also operable to process impedance signals from the electrically-conductive distal end of the needle instrument and the proximal electrode of the needle instrument, such as a guidewire, to thereby determine within the patient (PA) (i) whether the distal end of needle instrument is inside the guiding sheath or outside exposed to blood, (ii) if the distal end of the needle instrument has crossed the septum tissue; and (iii) location and direction of needle instrument. The electrical generator 306 can be configured to provide electrical energy to the distal electrode (1145) based at least in part on one or more impedances measured by the impedance monitoring module of the first driver module (14). Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from the navigation sensor assembly of the end effector of catheter assembly (100). For instance, as the end effector of catheter assembly (100) moves within the patient (PA), the corresponding position data from the navigation sensor assembly may cause the processor of console (12) to update the patient anatomy views in display (18) in real time to depict the regions of patient anatomy around the end effector as the end effector moves within the patient (PA). Moreover, the processor of console (12) may drive display (18) to show locations of aberrant conductive tissue sites, as detected via electrophysiological (EP) mapping with the end effector of catheter assembly (100) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of the end effector of catheter assembly (100) on the images of the patient's anatomy, such as by superimposing an illuminated dot, a crosshair, a graphical representation of the end effector, or some other form of visual indication. Such a superimposed visual indication may also move within the images of the patient anatomy on display (18) in real time as the physician moves the end effector of catheter assembly (100) within the patient (PA), thereby providing real-time visual feedback to the operator about the position of the end effector within the patient (PA) as the end effector moves within the patient (PA). The images provided through display (18) may thus effectively provide a video tracking the position of the end effector of catheter assembly (100) within a patient (PA), without necessarily having any optical instrumentation (i.e., cameras) viewing the end effector. In the same view, display (18) may simultaneously visually indicate the locations of aberrant conductive tissue sites detected through EP mapping. The physician (PH) may thus view display (18) to observe the real time positioning of the end effector of catheter assembly (100) in relation to the mapped aberrant conductive tissue sites and in relation to images of the adjacent anatomical structures in the patient (PA).

Fluid source (42) of the present example includes a bag containing saline or some other suitable fluid. Conduit (40) includes a flexible tube that is further coupled with a pump (44), which is operable to selectively drive fluid from fluid source (42) to catheter assembly (100). Such fluid may be expelled through openings of the distal tip member of the end effector of catheter assembly (100). Such fluid may be provided in any suitable fashion as will be apparent to those skilled in the art in view of the teachings herein.

II. Example of Guiding Sheath

In some procedures, the physician (PH) may wish to introduce a catheter of catheter assembly (100) into the patient (PA) via a guiding sheath. In some such procedures, the guiding sheath may be inserted into the patient (PA) (e.g., via the leg or groin of the patient (PA)); and then be advanced along a vein or artery to reach a position in or near the heart (H). Once the guiding sheath is suitably positioned in the patient (PA), the physician (PA) may then advance the end effector and catheter of catheter assembly (100) into the guiding sheath until the end effector exits the distal end of the guiding sheath. The physician (PA) may then operate catheter assembly (100) to provide EP mapping, ablation, or any other kind of operations in or near the heart (H) of the patient (PA).

Figure 2:
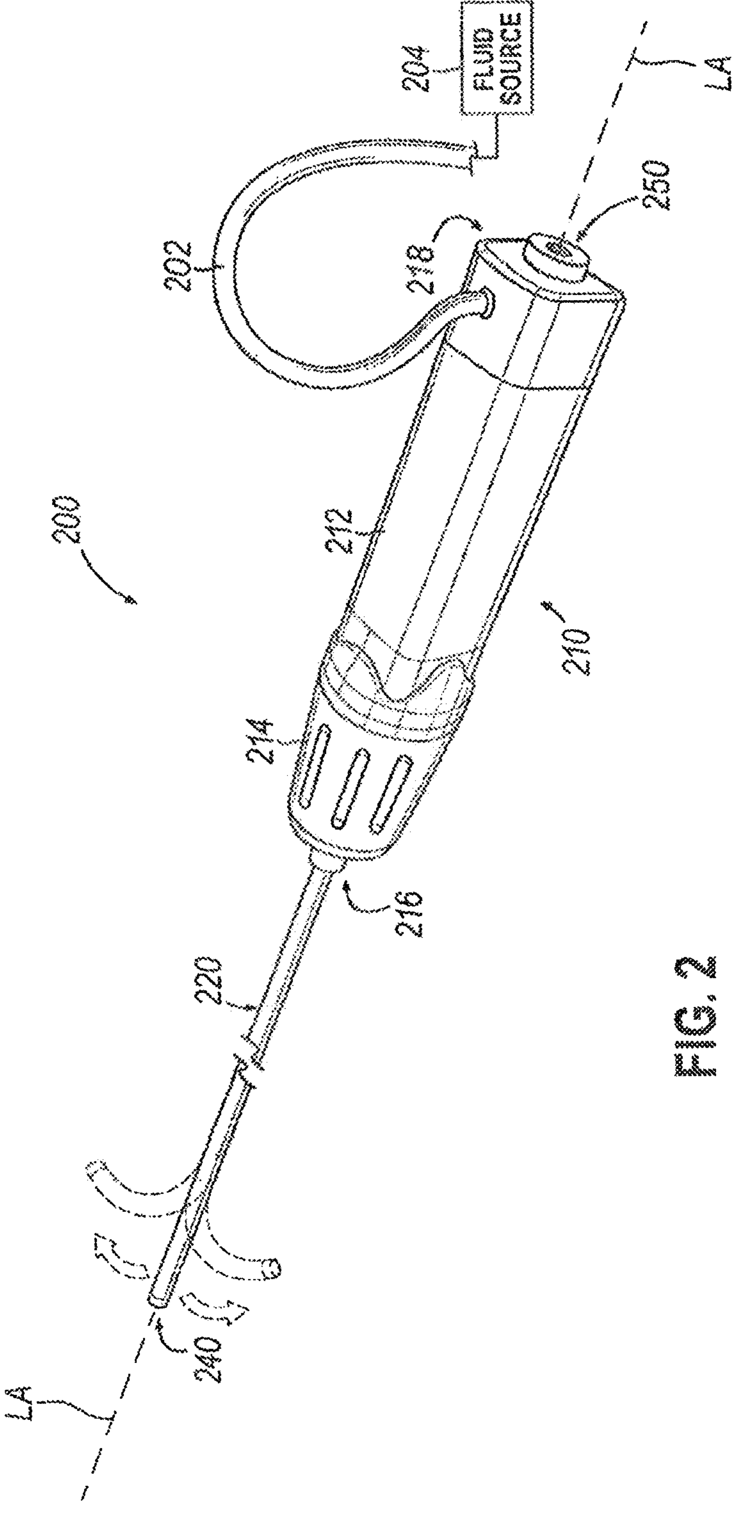
FIG. 2 depicts a perspective view of an example of a guiding sheath that may be used with the catheter assembly of FIG. 1.

FIG. 2 shows an example of a guiding sheath (200) that may be used in such procedures. Guiding sheath (200) of this example includes a body in the form of a handle assembly (210) with a hollow shaft (220) extending distally from a distal end (216) of handle assembly (210). Handle assembly (210) is configured for grasping by a casing (212). The open distal end (240) of the hollow shaft (220) is operable to deflect laterally away from a longitudinal axis (LA) of the shaft. This deflection is controlled by a rotary knob (214) at distal end (216) of handle assembly (210). Rotary knob (214) is rotatable relative to casing (212), about the longitudinal axis (LA), to thereby actuate components that drive lateral deflection of open distal end (240) of hollow shaft (220). By way of example only, such actuation components may include one or more pull wires, bands, or any other suitable structures as will be apparent to those skilled in the art in view of the teachings herein. While the body of guiding sheath (200) is in the form of handle assembly (210) in this example, the body may take other forms. For instance, some variations may provide a robotically controlled form of guiding sheath (200). In some such variations, the body may take the form of a structure that mechanically interfaces with a robotic arm and/or other kind of robotic driving feature.

As shown in FIG. 2, a tube (202) extends laterally from the proximal end (218) of handle assembly (210). Tube (202) of this example is in fluid communication with a hollow interior (not shown) defined within handle assembly (210), with the hollow interior being in fluid communication with the interior of hollow shaft (220). Tube (202) of the present example is further in fluid communication with a fluid source (204). By way of example only, fluid source (204) may contain saline, a fluoroscopy contrast fluid, or any other suitable fluid. In some variations, fluid is communicated via an instrument that is disposed within hollow shaft (220), such as will be described in greater detail below in the context of needle instrument (290). In some such versions, tube (202) is omitted; and the instrument within hollow shaft (220) is directly coupled with fluid source (204).

As also shown in FIG. 2, proximal end (218) of handle assembly (210) further includes an insertion port (250). Insertion port (250) is aligned with the longitudinal axis (LA) and provides a port for inserting the end effector and catheter of catheter assembly (100) into hollow shaft (220). Insertion port (250) of this example includes an annular protrusion (252) defining an opening. Protrusion (252) protrudes proximally from casing (212) at proximal end (218). In some versions, protrusion (252) is omitted.

A seal (not shown) is positioned within the opening of insertion port (250). By way of example only, the seal may include an elastomeric membrane or other kind of component(s) as will be apparent to those skilled in the art in view of the teachings herein. The seal in the opening of insertion port (250) may further include a slit arrangement that is configured to facilitate insertion of an instrument (e.g., catheter of catheter assembly (100), etc.) through the seal. When nothing is inserted through the seal in the opening of insertion port (250), the seal is configured to provide a fluid-tight seal that prevents fluid from escaping the portion of the above-described fluid path defined within handle assembly (210) via insertion port (250); and prevents air from entering the above-described fluid path defined within handle assembly (210) via insertion port (250). When an instrument is inserted through the seal in the opening of insertion port (250), the seal still substantially maintains a fluid-tight seal of insertion port (250), preventing fluid from escaping the above-described fluid path defined within handle assembly (210) via insertion port (250); and preventing air from entering above-described fluid path defined within handle assembly (210) via insertion port (250), while still allowing the inserted instrument to translate relative to the seal in the opening of insertion port (250). Thus, regardless of whether an instrument is disposed in insertion port (250), the seal may prevent fluids from leaking out through insertion port (250) and prevent air from being aspirated into the heart (H) of the patient (PA) via insertion port (250).

III. Example of Transseptal Penetration in Heart

In some procedures, it may be desirable to have the end effector of catheter assembly (100) traverse the atrial septum in order to reach a targeted cardiovascular structure. For instance, the end effector may enter the heart (H) via the right atrium; while the targeted cardiovascular structure is a pulmonary vein, which is extends from the left atrium. With the atrial septum presenting an anatomical barrier between the right atrium and the left atrium, a perforating instrument may be used to form an opening through the atrial septum to thereby provide a passageway for the end effector of catheter assembly (100) to reach the left atrium and adjacent structures from the right atrium.

Figures 3A, 3B, 3C, 3D, 3E:
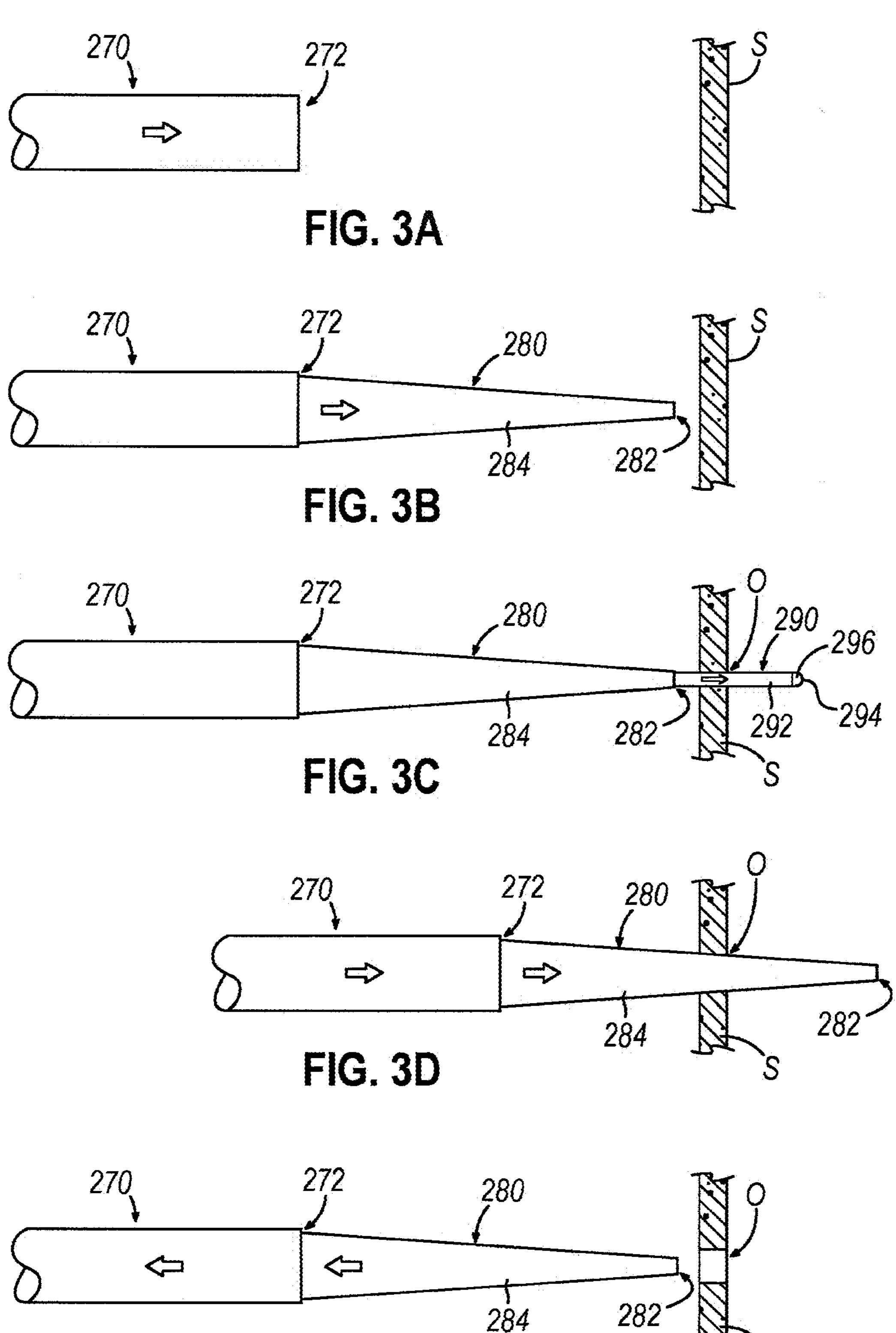
FIG. 3A depicts a schematic view of an example of a sheath approaching an atrial septum.
FIG. 3B depicts a schematic view of a dilator advanced distally relative to the sheath of FIG. 3A, such that the dilator is approaching the atrial septum.
FIG. 3C depicts a schematic view of a needle instrument advanced distally relative to the sheath of FIG. 3A and the dilator of FIG. 3B, such that the needle is penetrating the atrial septum to form an opening.
FIG. 3D depicts a schematic view of the dilator of FIG. 3B advanced distally through the opening formed by the needle instrument of FIG. 3C, such that the dilator is dilating the opening formed by the needle.
FIG. 3E depicts a schematic view of the dilator of FIG. 3B and the sheath of FIG. 3A retracted proximally, thereby exiting the dilated opening in the atrial septum.

FIG. 3A, FIG. 3B, FIG. 3C, FIG. 3D and FIG. 3E show an example of a procedure where a needle instrument (290) is used to form an opening (O) through an atrial septum (S); and a dilator (280) is used to enlarge the opening (O). As shown in FIG. 3A, the procedure begins with a sheath (270) that is positioned within the right atrium, such that an open distal end (272) of sheath (270) is oriented toward a penetration target location of the septum (S). By way of example only, sheath (270) may include a universal guiding sheath such as guiding sheath (200) described above; or may be a sheath that is configured specifically for use with dilator (280) and needle instrument (290) (e.g., as part of a kit, etc.).

Once distal end (272) of sheath (270) has been appropriately positioned, dilator (280) is advanced distally relative to sheath (270), such that dilator (280) protrudes distally from distal end (272) of sheath (270) as shown in FIG. 3B. Dilator (280) of this example has an open distal end (282) and a tapered outer surface (284) that narrows toward distal end (282). In some versions, tapered outer surface (284) has a linear taper. In some other versions, tapered outer surface (284) has a curved taper. Alternatively, tapered outer surface (284) may have any other suitable configuration. With dilator (280) advanced distally relative to sheath (270), distal end (282) of dilator (280) is oriented toward the penetration target location of the septum (S).

Once distal end (282) of dilator (280) has been appropriately positioned, needle instrument (290) is advanced distally relative to dilator (280), such that a distal shaft (292) of needle instrument (290) protrudes distally from distal end (282) of dilator (280) as shown in FIG. 3C. As needle instrument (290) is advanced distally relative to dilator (280), a distal tip (294) and a portion of distal shaft (262) of needle instrument (290) penetrate the septum (S), thereby forming an opening (O). In the present example, distal tip (294) has a blunt configuration. For instance, distal tip (294) may have a dome shape or any other suitable configuration. Thus, while the term "needle" is used in the term needle instrument (290), this should not be read as requiring needle instrument (290) to have a sharp distal tip (294) (though some versions of needle instrument (290) may in fact have a sharp distal tip (294)). Distal tip (294) of the present example further includes an electrode (296), which is activated to apply electrical energy (e.g., radiofrequency (AC type) or pulsed field (DC type) energy) to the tissue of the septum (S), to thereby assist in penetration of the septum (S). While one electrode (296) is shown, distal tip (294) may alternatively include two or more electrodes (296).

After needle instrument (290) has formed the opening (O), dilator (280) is advanced distally into the opening (O) as shown in FIG. 3D. In the example shown in FIG. 3D, needle instrument (290) is retracted proximally back into dilator (280) before dilator (280) is advanced distally into the opening (O). In some other scenarios, needle instrument (290) remains distally advanced relative to dilator (280) when dilator (280) is advanced distally into the opening (O). As also shown in FIG. 3D, sheath (270) is advanced distally with dilator (280) when dilator (280) is advanced distally into the opening (O). In some other scenarios, sheath (270) remains stationary while dilator (280) is advanced distally into the opening (O). Regardless of the relative positioning of sheath (270) and needle instrument (290) when dilator (280) is advanced distally into the opening (O), tapered outer surface (284) of dilator (280) bears against the inner edge of the opening (O), thereby dilating the opening (O).

Once dilator (280) has sufficiently dilated the opening (O), dilator (280) is retracted proximally relative to the opening (O), such that dilator (280) exits the dilated opening (O), as shown in FIG. 3E. In the example shown, sheath (270) is retracted proximally with dilator (280). In some scenarios, dilator (280) and needle instrument (290) are completely removed from sheath (270) after reaching the state shown in FIG. 3E, while sheath (270) remains disposed in the right atrium. Then, an additional instrument (e.g., cardiac mapping catheter, cardiac ablation catheter, etc.) may be inserted through sheath (2

70) and then through the dilated opening (O). In some other scenarios, sheath (270) is removed from the right atrium and another sheath (e.g., guiding sheath (200)) is introduced into the right atrium; with additional instrumentation (e.g., cardiac mapping catheter, cardiac ablation catheter, etc.) being advanced through that other sheath to ultimately pass through the dilated opening (O).

By way of example only, the end effector of catheter assembly (100) may be advanced from the right atrium through the dilated opening (O) to thereby position the end effector of catheter assembly (100) in the left atrium, in a pulmonary vein, and/or in any other suitable anatomical region on that side of the septum (S). In some scenarios, sheath (270), or hollow shaft (220) of guiding sheath (200), is passed through the dilated opening (O) to further assist in guiding the end effector of catheter assembly (100) into the left atrium, into a pulmonary vein, and/or into any other suitable anatomical region on that side of the septum (S). At the completion of the procedure, the opening (O) may be closed using any suitable techniques.

In addition to the foregoing, or in the alternative to the foregoing, needle instrument (290) may be configured and operable in accordance with at least some of the teachings of U.S. Pat. Nos. 6,994,094; 8,152,829; 9,848,943; U.S. Pub. No 2004/0220471; and/or U.S. Pub. No 2004/0220461. The disclosures of each of these references is incorporated by reference herein, in its entirety. Some dilators (280) and/or needle instruments (290) may also include one or more pull-wires and/or other features that provide steerability to the distal end of dilator (280) and/or needle instrument (290). Some such versions may thus provide an additional degree of steerability after distal end (280) of dilator (280) and/or distal tip (2 of the instrument exits open distal end (240) of hollow shaft (220). Some transseptal needle instruments may also include a wire at tip (264), to assist in providing primary engagement and lead-in for tip (264) into the atrial septum (S).

It is noted that a transseptal puncture apparatus outfitted with an energized tip, while described in specific reference to needle and guidewire examples herein, may alternatively take other forms. For instance, features of a needle as described herein may be applied to a guidewire; and features of a guidewire as described herein may be applied to a needle. The differences in construction between a guidewire or needle will pertain primarily to the materials and construction of the shaft, with the choice between guidewire versus needle for transseptal access being primarily a function of physician preference. Accordingly, as used herein a "transseptal puncture apparatus" or "transseptal apparatus" means either a guidewire or a needle having the tip features described herein within the scope of appended claims.

IV. Examples of Electrically-Conductive or Energized Transseptal Puncture Instruments In some procedures, it may be desirable to form the opening (O) through the atrial septum (S) via application of electrical energy (e.g., RF or IRE, etc.) to the tissue of the septum (S), such as to form the opening (O) without using a needle having a sharp distal tip and thereby eliminate the risk of such a sharp distal tip undesirably engaging with a wall or other structure of the heart (H) that is past the atrial septum (S) due to inadvertent over-advancement of the needle. Such electrical energy may include radiofrequency (AC type) electrical energy, pulsed field (DC type) electrical energy (e.g., irreversible electroporation, etc.), or some other form of electrical energy. In addition, or alternatively, it may be desirable to reduce the number of instruments inserted through hollow shaft (220) of guiding sheath (200) during a procedure, such as to reduce the number of instrument exchanges performed during the procedure and thereby reduce the risk of air being aspirated into the heart (H) of the patient (PA). Each of the examples of transseptal puncture instruments (300), dilators (302, 402, 502, 602, 702, 802), and guidewires (304, 904, 1004) described below may function in such a manner.

Figure 4A:
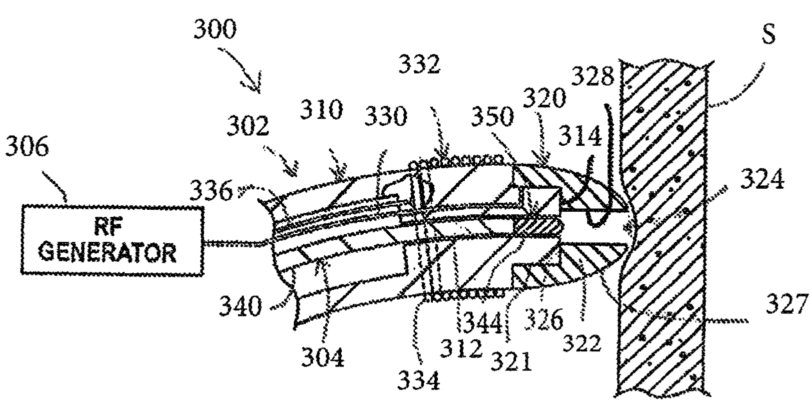
FIG. 4A depicts a cross-sectional side view of a distal portion of an example of a transseptal puncture instrument including a dilator and a guidewire, with a distal tip member of the dilator adjacent an atrial septum, and with the guidewire in a proximal position.
Figure 4B:
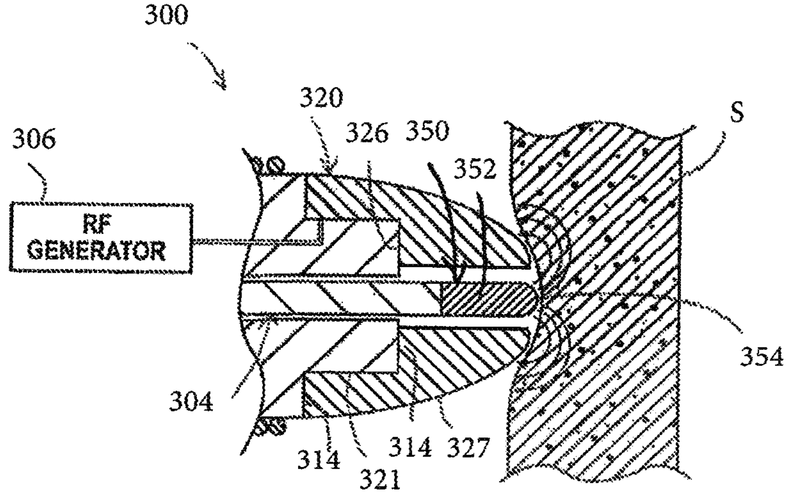
FIG. 4B depicts a cross-sectional side view of the distal portion of the transseptal puncture instrument of FIG. 4A, such that a distal tip member of the guidewire is adjacent the atrial septum, showing application of energy to the tissue of the atrial septum via the catheter distal tip member and the guidewire distal tip member to form an opening through the atrial septum.
Figure 4C:
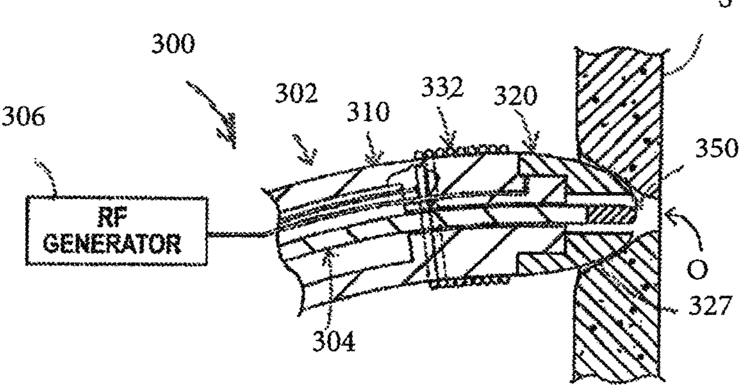
FIG. 4C depicts a cross-sectional side view of the distal portion of the transseptal puncture instrument of FIG. 4A, with the dilator advancing distally through the opening to expand the opening.

A. Example of Transseptal Puncture Instrument with Electrically-Energized Tip Member and Guidewire Tip Member FIG. 4A, FIG. 4B and FIG. 4C show a distal portion of an example of an instrument (300) that may be used to deliver electrical energy to tissue of an atrial septum (S) to form an opening (O) therethrough and that may also be used to dilate the opening (O). Instrument (300) of this example includes a dilator (302) and a guidewire (304) slidably housed within dilator (302) such that guidewire (304) and dilator (302) are extendable and retractable relative to each other. For example, guidewire (304) may be extendable and retractable relative to dilator (302) between a proximal position (FIG. 4A) and a distal position (FIG. 4B). In some versions, instrument (300) may include a handle assembly (not shown), which may be similar to handle assembly (110). The handle assembly may include any suitable actuation features for driving translation of dilator (302) and/or guidewire (304) relative to each other and/or relative to a handle body of the handle assembly, including but not limited to a slider, a pivoting rocker, a dial, etc. Instrument (300) may be coupled with an electrical generator (306), which may be operable to generate electrosurgical energy (e.g., RF or pulsed high-voltage DC, etc.) for delivery to the tissue of the septum (S) via instrument (300) to form the opening (O), as described in greater detail below.

Dilator (302) of this example includes a shaft (310) defining a lumen (312) that is configured to slidably receive guidewire (304) and that extends distally to a distal end (314) of shaft (310). Shaft (310) is sized for insertion through insertion port (250) and hollow shaft (220) of guiding sheath (200). Guiding sheath (200) may thus be used to assist in positioning a dilator tip member (320) of dilator (302) in relation to a target puncture location of the septum (S) in a manner generally similar to that described above with reference to FIG. 3A. Shaft (310) may comprise a metallic material, a plastic material, and/or any other suitable kind(s) of material(s). Shaft (310) of the present example includes a generally annular distal receptacle (321) extending radially inwardly from a radially outer surface of shaft (310) and proximally from distal end (314) for facilitating coupling of dilator tip member (320) to shaft (310), as described in greater detail below.

Dilator tip member (320) of the present example includes a body (322) having an open distal tip (324) and a proximal socket (326). Body (322) of the present example has a dome shape, such that distal tip (324) is atraumatic. More particularly, body (322) includes an exterior dilation surface (327) which curves radially inwardly toward distal tip (324) to define the illustrated dome shape. In some other versions, distal tip (324) may have any other suitable atraumatic configuration. In addition, or alternatively, dilation surface (327) may have any other suitable distally narrowing configuration. For example, dilation surface (327) may taper radially inwardly toward distal tip (324) to define a frustoconical shape (not shown). Proximal socket (326) of dilator tip member (320) receives distal end (314) of shaft (310) and is fixedly secured to shaft (310) such that a proximal portion of dilator tip member (320) is received within receptacle (321) of shaft (310).

By way of example only, dilator tip member (320) may be welded to shaft (310), soldered to shaft (310), adhered to shaft (310) using an adhesive or epoxy, press-fit onto shaft (310), and/or fixedly secured to shaft (310) in any other suitable fashion. In some variations, shaft (310) may include an exterior dilation surface (not shown) which narrows (e.g., curves or tapers radially inwardly) toward distal end (314) to provide a smooth transition from such an exterior dilation surface of shaft (310) to exterior dilation surface (327) of dilator tip member (320).

Body (322) of dilator tip member (320) further defines a lumen (328) that is coaxial with lumen (312) of shaft (310) and that is configured to slidably receive guidewire (304). Thus, lumen (328) provides a pathway for guidewire (304) that is distally advanced through lumen (312) to protrude distally from distal end (314) of shaft (310) or otherwise be exposed relative to distal end (314) of shaft (310). This enables guidewire (304) to reach the tissue of the septum (S). In the present example, lumen (328) has a diameter that is sufficiently larger than the diameter of tip member (350) of guidewire (304), to prevent inadvertent contact between tip member (350) and the sidewall of lumen (328). This may prevent short circuiting between tip member (320) and tip member (350), as will be understood in view of the description below.

Dilator tip member (320) of the present example is formed of an electrically conductive material. In this regard, dilator tip member (320) may be formed of any suitable material or combination of materials including but not limited to metallic conductive materials such as copper, gold, steel, aluminum, silver, nitinol, etc. and/or non-metallic conductive materials such as conducting polymers, silicides, graphite, etc.

As shown in FIG. 4A, FIG. 4B and FIG. 4C, dilator tip member (320) is coupled with electrical generator (306) via at least one first electrically conductive wire (330) extending along shaft (310) to electrically couple dilator tip member (320) with electrical generator (306). In some versions, first wire (330) may extend along shaft (310) in another lumen (not shown) that is isolated from lumen (312) to prevent first wire (330) from interfering with passage of guidewire (304) therethrough. While first wire (330) is shown, it will be appreciated that dilator tip member (320) may be electrically coupled with electrical generator (306) via any other suitable electrically conductive element(s), such as via one or more electrically conductive traces (e.g., of a flex circuit, etc.) extending along shaft (310) or one or more other electrical conductors embedded directly into shaft (310). Dilator tip member (320) is thus operable to apply electrical energy to the tissue of the septum (S) to form the opening (O) as described in greater detail below. In some versions where dilator tip member (320) is formed of a metallic material, the dilator tip member (320) may serve as a single, monopolar electrode, such that a ground pad may contact the patient (PA) to provide a return path for the electrical energy, whether RF and/or pulsed DC or otherwise. In some such versions, particularly where shaft (310) is formed of an electrically conductive material, an electrically insulating material may be interposed between dilator tip member (320) and shaft (310).

Alternatively, dilator tip member (320) may include one or more electrically conductive elements secured to distal tip (324), with such electrically conductive elements serving as electrodes that are configured to deliver electrical energy to the tissue of the septum (S) (e.g., with an electrically insulating material being interposed between the conductive element(s) and body (322)). For example, a pair of arcuate conductive elements may be angularly spaced apart from each other on distal tip (324) of dilator tip member (320).

Such conductive element(s) may each include any one or more of a conductive wire, plate, film, and/or coating, and may be formed of any suitable material or combination of materials including but not limited to metallic conductive materials such as copper, gold, steel, aluminum, silver, nitinol, etc. and/or non-metallic conductive materials such as conducting polymers, silicides, graphite, etc. Such conductive element(s) may be secured to distal tip (324) in any suitable fashion, including but not limited to being secured via an adhesive, via vapor deposition, or otherwise, and may be electrically coupled with electrical generator (306) via first wire (330) extending along shaft (310).

In cases where a pair of conductive elements is provided on distal tip (324), a corresponding pair of wires (330) may extend along shaft (310), and the pair of conductive elements may thereby be operable to apply bipolar electrical energy (e.g., RF or IRE) to the tissue of the septum (S), with one conductive element serving as an active electrode and the other conductive element serving as a return electrode to ablate the tissue, for example. In some versions, such conductive element(s) are configured and operable in accordance with at least some of the teachings of U.S. patent application Ser. No. 17/557,256, entitled "ENT Instrument with Deformable Guide having Translatable Imaging Feature," filed Dec. 21, 2021, the disclosure of which is incorporated by reference herein, in its entirety.

In the example shown, dilator (302) includes at least one navigation sensor assembly (332) fixedly secured to shaft (310) that is operable to generate signals that are indicative of the position and orientation of shaft (310) and/or dilator tip member (320) within the patient (PA). Navigation sensor assembly (332) includes at least one electromagnetic coil (334) operable to generate signals indicative of the position of the respective coil (334) and thereby indicative of the position of a portion of shaft (310) in three-dimensional space when positioned within an alternating electromagnetic field generated by field generators (20). The position data generated by such position related signals may be processed by the processor of console (12) for providing a visual indication to the operator to show the operator where shaft (310) and/or dilator tip member (320) of dilator (302) is located within the patient (P) in real time. Such a visual indication may be provided as an overlay on one or more preoperatively obtained images (e.g., CT scans) of the patient's anatomy.

In addition, or alternatively, the position data generated by position related signals from navigation sensor assembly (332) may be processed by the processor of console (12) to generate a current-to-position mapping (CPM) matrix. By way of example only, such a CPM matrix may be generated in accordance with at least some of the teachings of U.S. Pat. No. 10,398,347, entitled "Sheath Visualization Method by Means of Impedance Localization and Magnetic Information," issued Sep. 3, 2019, the disclosure of which is incorporated by reference herein, in its entirety; and/or U.S. Pat. No. 8,478,383, entitled "Probe Tracking Using Multiple Tracking Methods," issued Jul. 2, 2013, the disclosure of which is incorporated by reference herein, in its entirety.

Navigation sensor assembly (332) may be configured as a single-axis sensor (SAS) (e.g., having a single electromagnetic coil (334) wound about a single axis), as a dual-axis sensor (DAS) (e.g., having two electromagnetic coils (334) wound about respective axes), or as a triple-axis sensor (TAS) (e.g., having three electromagnetic coils (334) wound about respective axes). In addition, or alternatively, navigation sensor assembly (332) may be configured as a flexible printed circuit board (PCB). By way of example only, navigation sensor assembly (332) may be configured and operable in accordance with at least some of the teachings of U.S. patent application Ser. No. 17/584,693, entitled "Flexible Sensor Assembly for ENT Instrument," filed Jan. 26, 2022, the disclosure of which is incorporated by reference herein, in its entirety; and/or U.S. Pat. App. No. 17,547,517, entitled "Electrical Paths Along Flexible Section of Deflectable Sheath," filed Dec. 10, 2021, the disclosure of which is incorporated by reference herein, in its entirety. In some such cases, navigation sensor assembly (332) may include one or more active current location (ACL) electrodes in addition to or in lieu of the aforementioned electromagnetic coil sensors.

While navigation sensor assembly (332) of the example shown is fixedly secured to an exterior surface of shaft (310), it will be appreciated that navigation sensor assembly (332) may be fixedly secured to any suitable portion of shaft (310). For example, navigation sensor assembly (332) may be housed within shaft (310), such as disposed within lumen (312) while permitting passage of guidewire (304) therethrough. In the example shown, navigation sensor assembly (332) is configured to be coupled with guidance and drive system (10) via at least one second electrically conductive wire (336) extending along shaft (310) to electrically couple navigation sensor assembly (332) with guidance and drive system (10). In some versions, second wire (336) may extend along shaft (310) in another lumen (not shown) that is isolated from lumen (312) to prevent second wire (336) from interfering with passage of guidewire (304) therethrough.

While second wire (336) is shown, it will be appreciated that navigation sensor assembly (332) may be electrically coupled with guidance and drive system (10) via any other suitable electrically conductive element(s), such as via one or more electrically conductive traces (e.g., of a flex circuit, etc.) extending along shaft (310) or one or more other electrical conductors embedded directly into shaft (310). In some cases, navigation sensor assembly (332) may be omitted. In some such cases, at least a distal portion of dilator (302) (e.g., including dilator tip member (320)) may be echogenic to facilitate visualization of at least the distal portion of dilator (302) via ultrasound.

Guidewire (304) of this example includes an elongate member (340) extending to a distal end (344). Elongate member (340) may include a shaft or a coil, for example. In cases where elongate member (340) includes a coil, the coil may be wrapped about a core wire (not shown), which may be secured relative to distal end (344) and prevent the coil from elongating when the coil is placed under tensile stress. Elongate member (340) is sized for insertion through lumens (312, 328) of dilator (302). Dilator (302) may thus be used to assist in positioning a tip member (350) of guidewire (304) in relation to a target puncture location of the septum (S).

Guidewire tip member (350) of the present example includes a body (352) having a distal tip (354). Distal tip (354) of the present example has a dome shape, such that distal tip (354) is atraumatic. In some other versions, distal tip (354) may have any other suitable atraumatic configuration. Guidewire tip member (350) is fixedly secured to elongate member (340) at or near distal end (344) of elongate member (340). For example, body (352) may include a proximal socket (not shown) that receives distal end (344) of elongate member (340) and is fixedly secured to elongate member (340). By way of example only, guidewire tip member (350) may be welded to elongate member (340), soldered to elongate member (340), adhered to elongate member (340) using an adhesive or epoxy, press-fit onto elongate member (340), and/or fixedly secured to elongate member (340) in any other suitable fashion.

Guidewire tip member (350) of the present example is formed of an electrically conductive material. In this regard, guidewire tip member (350) may be formed of any suitable material or combination of materials including but not limited to metallic conductive materials such as copper, gold, steel, aluminum, silver, nitinol, etc. and/or non-metallic conductive materials such as conducting polymers, silicides, graphite, etc.

Guidewire tip member (350) may be coupled with electrical generator (306) via one or more wires, traces (e.g., of a flex circuit, etc.), or other electrically conductive elements (not shown) extending along elongate member (340) to electrically couple guidewire tip member (350) with electrical generator (306). Guidewire tip member (350) is thus operable to apply electrical energy to the tissue of the septum (S) to form the opening (O) as described in greater detail below. In some versions where guidewire tip member (350) is formed of a metallic material, the guidewire tip member (350) may serve as a single, monopolar electrode, such that a ground pad may contact the patient (PA) to provide a return path for the electrical energy. In some such versions, particularly where elongate member (340) is formed of an electrically conductive material, an electrically insulating material may be interposed between guidewire tip member (350) and elongate member (340).

Alternatively, guidewire tip member (350) may include one or more electrically conductive elements secured to distal tip (354) and configured to deliver electrical energy to the tissue of the septum (S) (e.g., with an electrically insulating material being interposed between the conductive element(s) and body (352)). For example, a pair of arcuate conductive elements may be angularly spaced apart from each other on distal tip (354) of guidewire tip member (350). Such conductive element(s) may each include any one or more of a conductive wire, plate, film, and/or coating, and may be formed of any suitable material or combination of materials including but not limited to metallic conductive materials such as copper, gold, steel, aluminum, silver, nitinol, etc. and/or non-metallic conductive materials such as conducting polymers, silicides, graphite, etc. Such conductive element(s) may be secured to distal tip (354) in any suitable fashion, including but not limited to being secured via an adhesive, via vapor deposition, or otherwise, and may be electrically coupled with generator (306) via the one or more wires, traces, or other electrically conductive elements extending along elongate member (340).

In cases where a pair of conductive elements is provided on distal tip (354), a corresponding pair of wires may extend along elongate member (340), and the pair of conductive elements may thereby be operable to apply bipolar electrical energy to the tissue of the septum (S), with one conductive element serving as an active electrode and the other conductive element serving as a return electrode to ablate the tissue, for example. In some versions, such conductive element(s) are configured and operable in accordance with at least some of the teachings of U.S. Pub. No. 2022/0110513, entitled "ENT Instrument with Deformable Guide having Translatable Imaging Feature," published Apr. 14, 2022, the disclosure of which is incorporated by reference herein, in its entirety. In addition to, or in lieu of, being capable of providing bipolar electrical energy by itself, guidewire tip member (350) may cooperate with dilator tip member (320) to provide bipolar electrical energy as described below.

By way of example only, guidewire (304) may be configured and operable in accordance with at least some of the teachings of U.S. Pat. No. 11,213,344, entitled "Guidewire with Ablation and Coagulation Functionality," issued Jan. 4, 2022, the disclosure of which is incorporated by reference herein, in its entirety; U.S. Pat. No. 10,603,472, entitled "Guidewires Having Improved Mechanical Strength and Electromagnetic Shielding," issued Mar. 31, 2020, the disclosure of which is incorporated by reference herein, in its entirety; and/or U.S. Pub. No. 2021/0196370, entitled "Neurosurgery Guidewire with Integral Connector for Sensing and Applying Therapeutic Electrical Energy," published Jul. 1, 2021, the disclosure of which is incorporated by reference herein, in its entirety.

In some versions, guidewire (304) includes at least one navigation sensor assembly (not shown) fixedly secured to elongate member (340) that is operable to generate signals (e.g., in response to the presence of an alternating electromagnetic field generated by field generators (20)) that are indicative of the position and orientation of elongate member (340) and/or guidewire tip member (350) within the patient (PA), such as in a manner similar to that described above.

In the example shown, dilator tip member (320) (or the conductive element(s) thereof) and guidewire tip member (350) (or the conductive element(s) thereof) are configured to cooperate with each other to apply bipolar electrical energy to the tissue of the septum (S). For instance, guidewire tip member (350) (or the conductive element(s) thereof) may serve as an active electrode while dilator tip member (320) (or the conductive element(s) thereof) serves as a return electrode. Alternatively, dilator tip member (320) (or the conductive element(s) thereof) may serve as an active electrode while guidewire tip member (350) (or the conductive element(s) thereof) serves as a return electrode. In either arrangement, such application of bipolar electrical energy to the tissue of the septum (S) may be sufficient to form the opening (O) therethrough.

It will be appreciated that such application of bipolar electrical energy for forming the opening (O) may be performed with relatively low power, at least by comparison to application of monopolar electrical energy via either dilator tip member (320) or guidewire tip member (350) for forming the opening (O). This may be due to the relatively short path along which the current travels between dilator tip member (320) and guidewire tip member (350), at least by comparison to the relatively long path along which the current would travel between either dilator tip member (320) or guidewire tip member (350) and a ground pad, and/or due to the relatively low impedance of the tissue that the current travels through between dilator tip member (320) and guidewire tip member (350), at least by comparison to the relatively high impedance of the tissue that the current would travel through between either dilator tip member (320) or guidewire tip member (350) and the ground pad. As noted above, lumen (328) of tip member (320) has a diameter that is sufficiently larger than the diameter of tip member (350) of guidewire (304), to prevent inadvertent contact between tip member (350) and the sidewall of lumen (328). This may prevent short circuiting between tip member (320) and tip member (350), particularly when one or both of tip members (320, 350) is/are activated to apply electrical energy.

In an example of use of instrument (300), dilator (302) may initially be inserted through guiding sheath (200) to engage dilator tip member (320) (or the conductive element(s) thereof) with the tissue at the target puncture location of the septum (S), while guidewire (304) may be in a retracted position relative to dilator (302), as shown in FIG. 4A. Then, the physician (PH) may advance guidewire (304) distally through dilator (302) to engage guidewire tip member (350) (or the conductive element(s) thereof) with the tissue at the target puncture location of the septum (S) and may subsequently activate generator (306), with dilator tip member (320) (or the conductive element(s) thereof) and guidewire tip member (350) (or the conductive element(s) thereof) serving as electrodes applying bipolar electrical energy to the tissue at the target puncture location of the septum (S) to form the opening (O) therethrough, as shown in FIG. 4B.

It will be appreciated that dilator tip member (320) (or the conductive element(s) thereof) and guidewire tip member (350) (or the conductive element(s) thereof) may be accurately positioned relative to the tissue at the target puncture location of the septum (S) based on the position data generated by the position related signals received from navigation sensor assembly (332) of dilator (302) and/or the navigation sensor assembly of guidewire (304). In some versions, dilator (302) and guidewire (304) may include complementary (e.g., interlocking) mechanical features for facilitating rotational and/or longitudinal positioning of dilator tip member (320) (or the conductive element(s) thereof) and guidewire tip member (350) (or the conductive element(s) thereof) relative to each other a predetermined manner for achieving the desired delivery of bipolar electrical energy. For example, dilator (302) and guidewire (304) may be configured to threadably engage each other to provide such predetermined relative positioning. In addition, or alternatively, dilator (302) and guidewire (304) may include corresponding indicia configured to align with each other to visually indicate such predetermined relative positioning; detent features to provide tactile feedback indicating appropriate relative positioning; and/or any other suitable features indicating appropriate relative positioning.

In some cases, the processor of console (12) may read cardiac electrical (e.g., EGMs, impedance change, etc.) signals from dilator tip member (320) (or the conductive element(s) thereof) and guidewire tip member (350) (or the conductive element(s) thereof) to confirm that dilator tip member (320) (or the conductive element(s) thereof) and guidewire tip member (350) (or the conductive element(s) thereof) are both sufficiently engaged with the tissue at the target puncture location of the septum (S) for the tissue to receive the bipolar electrical energy prior to activation of electrical generator (306). It will be appreciated that activation and/or deactivation of electrical generator (306) may be performed automatically by the processor of console (12), such as in response to feedback received by the processor of console (12) from dilator tip member (320) (or the conductive element(s) thereof) and guidewire tip member (350) (or the conductive element(s) thereof) to ensure proper ablation of the desired target tissue. In addition, or alternatively, such activation may be performed manually by the physician (PH), such as based on images or other information presented by display (18).

In some cases, the electrical impedance between dilator tip member (320) (or the conductive element(s) thereof) and guidewire tip member (350) (or the conductive element(s) thereof) may be periodically or continuously measured during the application of bipolar electrical energy the tissue at the target puncture location of the septum (S) to monitor the progress of the formation of the opening (O). For example, the impedance may be relatively high during ablation of the tissue at the target puncture location of the septum (S) as a result of tissue vaporization between dilator tip member (320) (or the conductive element(s) thereof) and guidewire tip member (350) (or the conductive element(s) thereof), and may substantially decrease upon the formation of the opening (O) when guidewire tip member (350) (or the conductive element(s) thereof) is no longer contacting and vaporizing through septal tissue. This substantial decrease in the impedance may thus provide an indication that the opening (O) has been successfully formed. In some versions, the processor of console (12) may automatically deactivate electrical generator (306) in response to the substantial decrease in the impedance, thereby preventing the risk of ablating a wall or other structure of the heart (H) that is past the atrial septum (S). In addition, or alternatively, display (18) may alert the physician (PH) that the opening (O) has been formed so that the physician (PH) may take appropriate action.

It will be appreciated that the application of bipolar electrical energy to the tissue at the target puncture location of the septum (S) may be performed while maintaining each of dilator tip member (320) and guidewire tip member (350) at substantially fixed locations relative to the target puncture location of the septum (S) or while urging dilator tip member (320) and/or guidewire tip member (350) only slightly distally (e.g., to maintain electrical contact with the tissue at the target puncture location of the septum (S)), such that the opening (O) may be formed without applying any mechanical force, or while applying only nominal mechanical force, against the tissue at the target puncture location of the septum (S). In other words, either no or only minimal mechanical force may be required to form the opening (O), thereby eliminating or mitigating the risk of inadvertently over-advancing instrument (300), at least during the initial formation of the opening (O). In cases where some mechanical force is applied against the tissue at the target puncture location of the septum (S), the atraumatic configurations of distal tip (324) and distal tip (354) may prevent injury to a wall or other structure of the heart (H) that is past the atrial septum (S) if such inadvertent over-advancement of dilator (302) and/or guidewire (304) occurs. In this regard, a determination that the opening (O) has been successfully formed may be based on the position data generated by the position related signals received from navigation sensor assembly (332) of dilator (302) and/or the navigation sensor assembly of guidewire (304), in addition to or in lieu of the aforementioned impedance-based determination.

As shown in FIG. 4C, the physician (PH) may in some cases advance dilator (302) distally through the opening (O) following the initial formation of the opening (O) to engage dilation surface (327) of dilator tip member (320) (and/or a dilation surface of shaft (310)) with the periphery of the opening (O) and thereby expand the opening (O). In addition, or alternatively, the physician (PH) may advance dilator (302) and/or guidewire (304) through the opening (O) to perform additional operations beyond the septum (S). For example, the physician (PH) may advance dilator (302) and/or guidewire (304) through the opening (O) to reach the left atrium of the heart (H) to provide EP mapping, ablation, or any other kind of additional operations in the left atrium. Such multi-purpose utilization of dilator (302) and/or guidewire (304) may allow the additional operation(s) to be performed immediately following the formation of the opening (O) without first requiring an instrument exchange; and may thereby reduce the risk of air being aspirated into the heart (H) of the patient (PA) and/or reduce the duration of the procedure.

In some cases, guidewire (304) may be advanced through the opening (O) immediately upon formation of the opening (O) to position guidewire tip member (350) within the left atrium to enable a CPM matrix to be generated for the left atrium (e.g., based on the position data generated by the position related signals received from the navigation sensor assembly of guidewire (304)). In addition, or alternatively, guidewire tip member (350) may serve as an anchor in the left atrium such that one or more additional instruments (e.g., catheter of catheter assembly (100), etc.) may be advanced distally over guidewire (304), through the opening (O), and into the left atrium.

In some cases, prior to inserting dilator (302) through guiding sheath (200) to the position shown in FIG. 4A, guidewire (304) may be inserted into a major vein or artery (e.g., the femoral artery) of the patient (PA) (e.g., via the leg or groin of the patient (PA)) and then advanced distally along the vein or artery to position guidewire tip member (350) within the right atrium of the heart (H) to serve as an anchor therein. Guiding sheath (200) may then be advanced distally along the vein or artery over guidewire (304) for facilitating the subsequent insertion of dilator (302) through guiding sheath (200) to the position shown in FIG. 4A.

Figure 6:
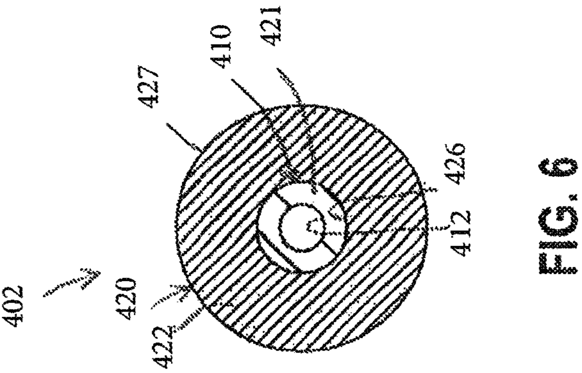
FIG. 6 depicts a cross-sectional end view of the dilator of FIG. 5, taken along line 6-6 of FIG. 5.
Figure 5:
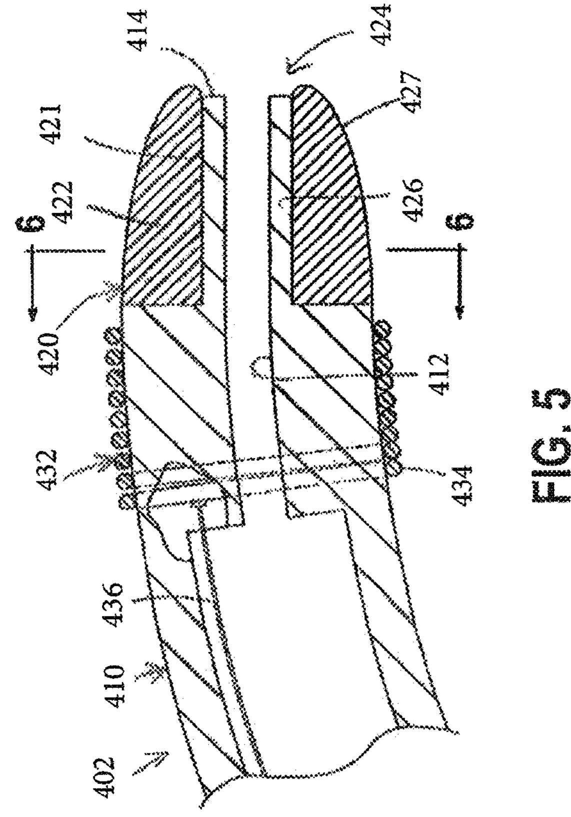
FIG. 5 depicts a cross-sectional side view of a distal portion of another example of a dilator for use with the transseptal puncture instrument of FIG. 4A and having a distal tip member configured to be electrically insulated from the guidewire distal tip member.

B. Example of Dilator with Electrically-Energized Tip Member Electrically Insulated from Guidewire Tip Member In some instances, it may be desirable to provide a dilator having an electrically insulating member interposed between the dilator tip member and the guidewire tip member, such as to inhibit electrical shorting between the dilator tip member and the guidewire tip member during electrical energization of the dilator tip member and the guidewire tip member. FIG. 5 and FIG. 6 show a distal portion of another example of a dilator (402) having such a configuration, and which may be incorporated into instrument (300) in place of dilator (302). Dilator (402) may be similar to dilator (302) described above except as otherwise described below. In this regard, dilator (402) of this example includes a shaft (410) defining a lumen (412) that is configured to slidably receive guidewire (304) and that extends distally to a distal end (414) of shaft (410). Shaft (410) is sized for insertion through insertion port (250) and hollow shaft (220) of guiding sheath (200). Guiding sheath (200) may thus be used to assist in positioning a dilator tip member (420) of dilator (402) in relation to a target puncture location of the septum (S) in a manner generally similar to that described above with reference to FIG. 3A. Shaft (410) of the present example includes a generally annular distal receptacle (421) extending radially inwardly from a radially outer surface of shaft (410) and proximally from distal end (414) for facilitating coupling of dilator tip member (420) to shaft (410).

In the example shown, at least a distal portion of shaft (410), such as the portion of shaft (410) that is radially inward of receptacle (421), comprises an electrically non-conductive (e.g., insulative) material, such as plastic, to electrically isolate dilator tip member (420) from objects within lumen (412). In this regard, dilator tip member (420) of the present example includes a body (422) having an open distal tip (424) and a longitudinal bore (426). Body (422) may be formed of an electrically conductive material, such that tip member (420) may serve as a monopolar electrode or as a bipolar electrode as described herein. Body (422) of the present example has a dome shape, such that distal tip (424) is atraumatic. More particularly, body (422) includes an exterior dilation surface (427) which curves radially inwardly toward distal tip (424) to define the illustrated dome shape. Dilator tip member (420) is received within receptacle (421) of shaft (410).

Dilator tip member (420) and, more particularly, bore (426), may have a length substantially equal to that of receptacle (421) of shaft (410) such that the portion of shaft (410) that is radially inward of receptacle (421) may be interposed between dilator tip member (420) and guidewire tip member (350) along substantially the entire length thereof to thereby inhibit electrical shorting between dilator tip member (420) and guidewire tip member (350) during electrical energization of dilator tip member (420) and guidewire tip member (350). In this regard, dilator tip member (420) may be coupled with electrical generator (306) via one or more wires, traces, or other electrically conductive elements (not shown) extending along shaft (410) to electrically couple dilator tip member (420) with electrical generator (306) in a manner similar to that described above in connection with FIG. 4A, FIG. 4B and FIG. 4C.

In the example shown, dilator (402) includes at least one navigation sensor assembly (432) fixedly secured to shaft (410) that is operable to generate signals that are indicative of the position and orientation of shaft (410) and/or dilator tip member (420) within the patient (PA). Navigation sensor assembly (432) includes at least one electromagnetic coil (434) operable to generate signals indicative of the position of the respective coil (434) and thereby indicative of the position of a portion of shaft (410) in three-dimensional space when positioned within an alternating electromagnetic field generated by field generators (20), in a manner similar to that described above. In the example shown, navigation sensor assembly (432) is configured to be coupled with guidance and drive system (10) via at least one electrically conductive wire (436) extending along shaft (410) to electrically couple navigation sensor assembly (432) with guidance and drive system (10). Alternatively, navigation sensor assembly (432) may be coupled with guidance and drive system (10) in any other suitable fashion. Similarly, navigation sensor assembly (432) may be positioned at any other suitable location(s) in relation to shaft (410).

Figure 7:
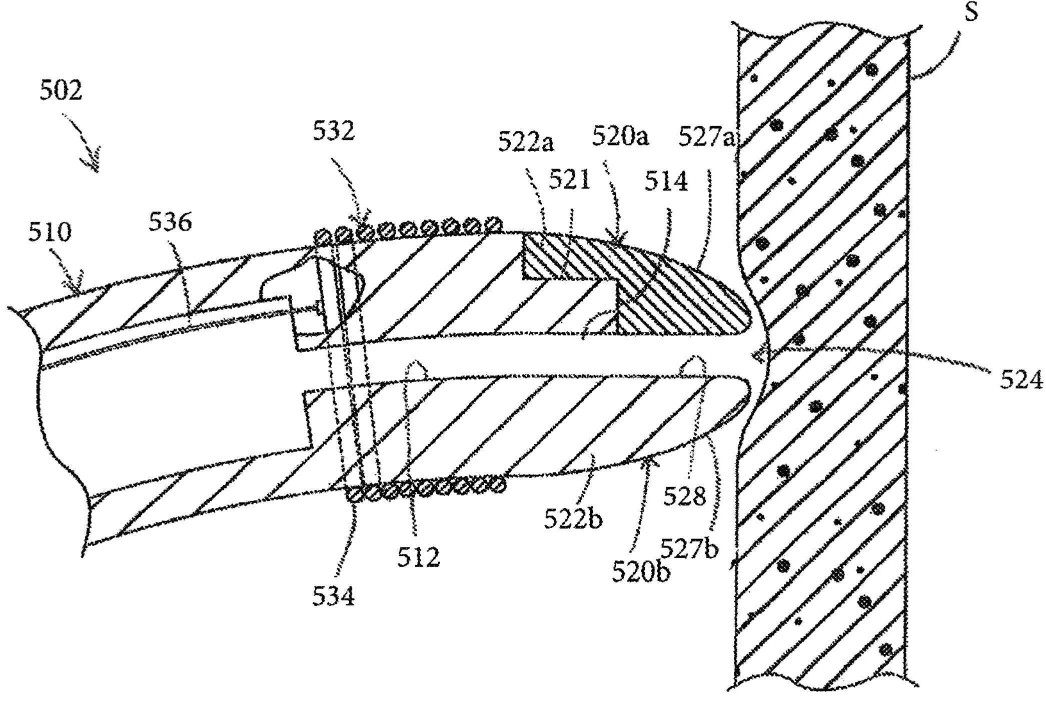
FIG. 7 depicts a cross-sectional side view of a distal portion of another example of a dilator for use with the transseptal puncture instrument of FIG. 4A and having an energized distal tip member on a single side of a guidewire lumen of the dilator.

C. Example of Dilator with Electrically-Energized Tip Member on Single Side of Guidewire Lumen In some instances, it may be desirable to provide a dilator having an electrically-energized tip member that is positioned on only a single side of the guidewire lumen, such as to inhibit coring of the septal tissue during electrical energization of the dilator tip member and the guidewire tip member. Providing a relatively small electrode (e.g., electrically-energized tip member) may also provide a higher energy density for the ablation/puncture. FIG. 7 shows a distal portion of another example of a dilator (502) having such a configuration, and which may be incorporated into instrument (300) in place of dilator (302). Dilator (502) may be similar to dilator (302) described above except as otherwise described below. In this regard, dilator (502) of this example includes a shaft (510) defining a lumen (512) that is configured to slidably receive guidewire (304) and that extends distally to a distal end (514) of shaft (510). Shaft (510) is sized for insertion through insertion port (250) and hollow shaft (220) of guiding sheath (200). Guiding sheath (200) may thus be used to assist in positioning a pair of dilator tip members (520*a*, 520*b*) of dilator (402) in relation to a target puncture location of the septum (S) in a manner generally similar to that described above with reference to FIG. 3A. Shaft (510) of the present example includes a generally semi-annular distal receptacle (521) extending radially inwardly from a radially outer surface of shaft (510) and proximally from distal end (514) for facilitating coupling of first dilator tip member (520*a*) to shaft (510), while second dilator tip member (520*a*) may be integrally formed together with shaft (510) as a unitary (e.g., monolithic) piece.

Each dilator tip member (520*a*, 520*b*) of the present example includes a body (522*a*, 522*b*). First body (522*a*) may be formed of an electrically conductive material, such that first dilator tip member (520*a*) may serve as a monopolar electrode or as a bipolar electrode as described herein. Each body (522*a*, 522*b*) is fixedly secured to distal end (514) of shaft (510) on respective sides of lumen (512) to collectively define an open distal tip (524) and a lumen (528) that is coaxial with lumen (512) of shaft (510). Lumen (528) is configured to slidably receive guidewire (304). Bodies (522*a*, 522*b*) of the present example collectively define a dome shape, such that distal tip (524) is atraumatic. More particularly, each body (522*a*, 522*b*) includes an exterior dilation surface (527*a*, 527*b*) which curves radially inwardly toward distal tip (524) to define the illustrated dome shape. Body (522*a*) of first dilator tip member (520*a*) has a proximal socket (526) which receives distal end (514) of shaft (510) and is fixedly secured to shaft (510) such that a proximal portion of first dilator tip member (520*a*) is received within receptacle (521) of shaft (510).

First dilator tip member (520*a*) may be coupled with electrical generator (306) via one or more wires, traces, or other electrically conductive elements (not shown) extending along shaft (510) to electrically couple first dilator tip member (520*a*) with electrical generator (306) in a manner similar to that described above in connection with FIG. 4A, FIG. 4B and FIG. 4C, and may thereby be operable to cooperate with guidewire tip member (350) to apply bipolar electrical energy to the tissue of the septum (S) on one side of lumen (528); while second dilator tip member (520*b*) remains unenergized such that electrical energy is not applied to the tissue of the septum (S) on the other side of lumen (528).

In the example shown, dilator (502) includes at least one navigation sensor assembly (532) fixedly secured to shaft (510) that is operable to generate signals that are indicative of the position and orientation of shaft (510) and/or dilator tip members (520*a*, 520*b*) within the patient (PA). Navigation sensor assembly (532) includes at least one electromagnetic coil (534) operable to generate signals indicative of the position of the respective coil (534) and thereby indicative of the position of a portion of shaft (510) in three-dimensional space when positioned within an alternating electromagnetic field generated by field generators (20), in a manner similar to that described above. In the example shown, navigation sensor assembly (532) is configured to be coupled with guidance and drive system (10) via at least one electrically conductive wire (536) extending along shaft (510) to electrically couple navigation sensor assembly (532) with guidance and drive system (10). Alternatively, navigation sensor assembly (532) may be coupled with guidance and drive system (10) in any other suitable fashion. Similarly, navigation sensor assembly (532) may be positioned at any other suitable location(s) in relation to shaft (510).

D. Example of Dilator with Pair of Adjacent Tip Members Surrounding Guidewire Lumen In some instances, it may be desirable to provide a dilator having a pair of adjacent tip members operable to apply bipolar electrical energy to tissue independently of the guidewire. FIG. 8 and FIG. 9 show a distal portion of another example of a dilator (602) having such a configuration, and which may be incorporated into instrument (300) in place of dilator (302). Dilator (602) may be similar to dilator (302) described above except as otherwise described below. In this regard, dilator (602) of this example includes a shaft (610) defining a lumen (612) that is configured to slidably receive guidewire (304) and that extends distally to a distal end (614) of shaft (610). Shaft (610) is sized for insertion through insertion port (250) and hollow shaft (220) of guiding sheath (200). Guiding sheath (200) may thus be used to assist in positioning a pair of dilator tip members (620*a*, 620*b*) of dilator (602) in relation to a target puncture location of the septum (S) in a manner generally similar to that described above with reference to FIG. 3A.

Each dilator tip member (620*a*, 620*b*) of the present example includes a body (622*a*, 622*b*). Each body (622*a*, 622*b*) may be formed of an electrically conductive material, such that each dilator tip member (620*a*, 620*b*) may serve as a monopolar electrode or as a bipolar electrode as described herein. Each body (622*a*, 622*b*) is fixedly secured to distal end (614) of shaft (610) on respective sides of lumen (612) to collectively define an open distal tip (624) and a lumen (628) that is coaxial with lumen (612) of shaft (610) and that is configured to slidably receive guidewire (304). Bodies (622*a*, 622*b*) of the present example collectively define a dome shape, such that distal tip (624) is atraumatic. More particularly, each body (622*a*, 622*b*) includes an exterior dilation surface (627*a*, 627*b*) which curves radially inwardly toward distal tip (624) to define the illustrated dome shape. As best shown in FIG. 9, bodies (622*a*, 622*b*) collectively have a circular cross-sectional shape that is coaxial with lumen (612) of shaft (610), such that bodies (622*a*, 622*b*) may collectively circumferentially surround a longitudinal axis of lumen (612).

Dilator tip members (620*a*, 620*b*) may each be electrically coupled with electrical generator (306) via respective wires (not shown) extending along shaft (610), such that dilator tip members (620*a*, 620*b*) may thereby be operable to apply bipolar electrical energy to the tissue of the septum (S), with one dilator tip member (620*a*, 620*b*) serving as an active electrode and the other dilator tip member (620*a*, 620*b*) serving as a return electrode to ablate the tissue, for example. In this manner, dilator (602) may be capable of forming the opening (O) independently of guidewire (304), such that guidewire tip member (350) may be omitted. In some cases, the ability of dilator (602) to form the opening (O) independently of guidewire (304) may allow lumen (612) to be closed at or near distal end (614) of shaft (610) such that lumen (612) may facilitate routing of wires along shaft (610) to dilator tip members (620*a*, 620*b*), for example; but may not provide a pathway for guidewire (304) to be distally advanced out through distal end (614) of shaft (610) or otherwise enable guidewire (304) to reach the tissue of the septum (S). In some other cases, the ability of dilator (602) to form the opening (O) independently of guidewire (304) may allow lumen (612) to be omitted.

While not shown in FIG. 8 and FIG. 9, dilator (602) may include a navigation sensor assembly like any other navigation sensor assembly described herein.

E. Example of Dilator with Pair of Adjacent Tip Members Offset from Guidewire Lumen In some instances, it may be desirable to provide a dilator having a pair of adjacent tip members operable to apply bipolar electrical energy to tissue independently of the guidewire and that are offset from the guidewire lumen, such as to inhibit coring of the septal tissue during electrical energization of the pair of tip members. FIG. 10 shows a distal portion of another example of a dilator (702) having such a configuration, and which may be incorporated into instrument (300) in place of dilator (302). Dilator (702) may be similar to dilator (602) described above except as otherwise described below. In this regard, dilator (702) of this example includes a shaft (not shown) defining a lumen (712) that is configured to slidably receive guidewire (304) and that extends distally to a distal end (not shown) of the shaft. Lumen (712) is laterally offset from the central longitudinal axis of the shaft in this example. Dilator (702) further includes a pair of dilator tip members (720*a*, 720*b*).

Each dilator tip member (720*a*, 720*b*) of the present example includes a body (722*a*, 722*b*). Each body (722*a*, 722*b*) may be formed of an electrically conductive material, such that each dilator tip member (720*a*, 720*b*) may serve as a monopolar electrode or as a bipolar electrode as described herein. Each body (722*a*, 722*b*) is fixedly secured to the distal end of the shaft on respective sides of lumen (712) to collectively define an open distal tip (not shown) and a lumen (728) that is coaxial with lumen (712) of the shaft and that is configured to slidably receive guidewire (304). Lumen (728) is thus also laterally offset from the central longitudinal axis of the shaft of dilator (702) in this example. Bodies (722*a*, 722*b*) of the present example may collectively have a dome shape, such that the distal tip is atraumatic. More particularly, each body (722*a*, 722*b*) includes an exterior dilation surface (727*a*, 727*b*) which may curve radially inwardly toward the distal tip to define such a dome shape. In the example shown, bodies (722*a*, 722*b*) collectively have a circular cross-sectional shape that is non-coaxial with lumen (712) of the shaft, such that bodies (722*a*, 722*b*) may not collectively circumferentially surround a longitudinal axis of lumen (712). In this manner, a lateral side of lumen (728) may be exposed such that lumen (728) may be generally C-shaped, to thereby inhibit septal tissue coring during electrical energization of dilator tip members (720*a*, 720*b*). In this regard, dilator tip members (720*a*, 720*b*) may each be electrically coupled with electrical generator (306) via respective wires (not shown) extending along shaft (710) in a manner similar to that described above in connection with FIG. 8 and FIG. 9.

While not shown in FIG. 10, dilator (702) may include a navigation sensor assembly like any other navigation sensor assembly described herein.

F. Example of Dilator with Pair of Coaxial Tip Members

Figures 11, 12:
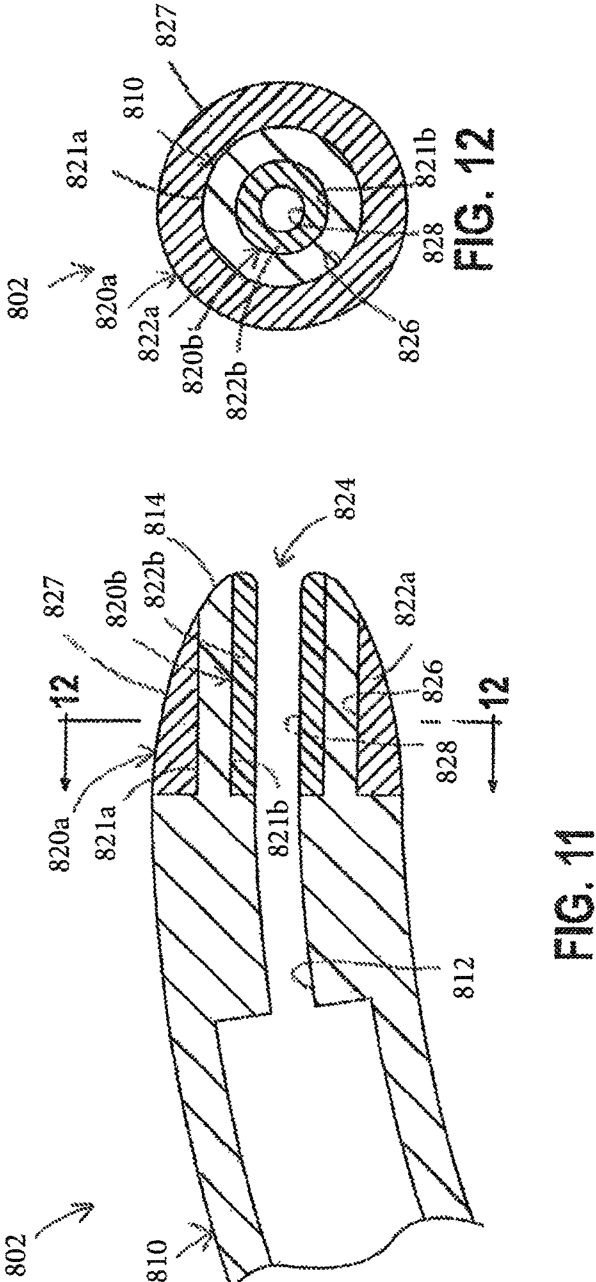
FIG. 11 depicts a cross-sectional side view of a distal portion of another example of a dilator for use with the transseptal puncture instrument of FIG. 4A and having a pair of coaxial distal tip members.
FIG. 12 depicts a cross-sectional end view of the dilator of FIG. 11, taken along line 12-12 of FIG. 11.

In some instances, it may be desirable to provide a dilator having a pair of coaxial tip members operable to apply bipolar electrical energy to tissue independently of the guidewire. FIG. 11 and FIG. 12 show a distal portion of another example of a dilator (802) having such a configuration, and which may be incorporated into instrument (300) in place of dilator (302). Dilator (802) may be similar to dilator (602) described above except as otherwise described below. In this regard, dilator (802) of this example includes a shaft (810) defining a lumen (812) that is configured to slidably receive guidewire (304) and that extends distally to a distal end (814) of shaft (810). Shaft (810) is sized for insertion through insertion port (250) and hollow shaft (220) of guiding sheath (200). Guiding sheath (200) may thus be used to assist in positioning a pair of dilator tip members (820*a*, 820*b*) of dilator (802) in relation to a target puncture location of the septum (S) in a manner generally similar to that described above with reference to FIG. 3A. Shaft (810) of the present example includes a first generally annular distal receptacle (821*a*) extending radially inwardly from a radially outer surface of shaft (810) and proximally from distal end (814) for facilitating coupling of first dilator tip member (820*a*) to shaft (810), and a second generally annular distal receptacle (821*b*) extending radially outwardly from lumen (812) and proximally from distal end (814) for facilitating coupling of second dilator tip member (820*b*) to shaft (810).

In the example shown, at least a distal portion of shaft (810), such as the portion of shaft (810) that is radially between receptacles (821*a*, 821*b*), comprises an electrically non-conductive (e.g., insulative) material, such as plastic, to electrically isolate dilator tip members (820*a*, 820*b*) from each other. In this regard, each dilator tip member (820*a*, 820*b*) of the present example includes a body (822*a*, 822*b*). Each body (822*a*, 822*b*) may be formed of an electrically conductive material, such that each dilator tip member (820*a*, 820*b*) may serve as a monopolar electrode or as a bipolar electrode as described herein. Each body (822*a*, 822*b*) is fixedly secured to distal end (814) of shaft (810) at respective radial distances from lumen (612). Second dilator tip member (820*b*) is received within second receptacle (821*b*) of shaft (810), and defines an open, atraumatic distal tip (824) and a lumen (828) that is coaxial with lumen (812) of shaft (810) and that is configured to slidably receive guidewire (304). Body (822*a*) of first dilator tip member (820*a*) of the present example has a dome shape, while body (822*b*) of second dilator tip member (820*b*) has a cylindrical shape. More particularly, body (822*a*) includes an exterior dilation surface (827) that curves radially inwardly toward distal tip (824) to define the illustrated dome shape. Body (822*a*) of first dilator tip member (820*a*) has a bore (826) and is received within first receptacle (821*a*) of shaft (810). As best shown in FIG. 12, bodies (822*a*, 822*b*) each have a circular cross-sectional shape and are coaxial with each other.

Dilator tip members (820*a*, 820*b*) may each be electrically coupled with electrical generator (306) via respective wires (not shown) extending along shaft (810), such that dilator tip members (820*a*, 820*b*) may thereby be operable to apply bipolar electrical energy to the tissue of the septum (S), with one dilator tip member (820*a*, 820*b*) serving as an active electrode and the other dilator tip member (820*a*, 820*b*) serving as a return electrode to ablate the tissue, for example. In this manner, dilator (802) may be capable of forming the opening (O) independently of guidewire (304).

While not shown in FIG. 11 and FIG. 12, dilator (802) may include a navigation sensor assembly like any other navigation sensor assembly described herein.

G. Example of Guidewire with Distal Portion Having Various Atraumatic Configurations In some instances, it may be desirable to provide a guidewire having a distal portion configured to assume a variety of atraumatic poses to prevent injury to a wall or other structure of the heart (H) that is past the atrial septum (S) if inadvertent over-advancement of the guidewire occurs. FIG. 13A, FIG. 13B, FIG. 13C and FIG. 13D show a distal portion of another example of a guidewire (904) having such a configuration, and which may be incorporated into instrument (300) in place of guidewire (304). Guidewire (904) may be similar to guidewire (304) described above except as otherwise described below. In this regard, guidewire (904) of this example includes an elongate member (940) extending to a distal end (944). Elongate member (940) may include a shaft or a coil, for example. In cases where elongate member (940) includes a coil, the coil may be wrapped about a core wire (not shown), which may be secured relative to distal end (944) and prevent the coil from elongating when the coil is placed under tensile stress. Elongate member (940) is sized for insertion through lumens (312, 328) of dilator (302). Dilator (302) may thus be used to assist in positioning a guidewire tip member (950) of guidewire (904) in relation to a target puncture location of the septum (S).

Guidewire tip member (950) of the present example includes a body (952) having a distal tip (954). Body (952) may be formed of an electrically conductive material, such that guidewire tip member (950) may serve as a monopolar electrode or as a bipolar electrode as described herein. Distal tip (954) of the present example has a dome shape, such that distal tip (954) is atraumatic. Guidewire tip member (950) is fixedly secured to elongate member (940) at or near distal end (944) of elongate member (940). For example, body (952) may include a proximal socket (not shown) that receives distal end (944) of elongate member (940) and is fixedly secured to elongate member (940). Guidewire tip member (950) may be coupled with electrical generator (306) via one or more wires, traces, or other electrically conductive elements (not shown) extending along elongate member (940) to electrically couple guidewire tip member (950) with electrical generator (306) in a manner similar to that described above in connection with FIG. 4A, FIG. 4B and FIG. 4C; and may thereby be operable to cooperate with dilator tip member (320) to apply bipolar electrical energy to the tissue of the septum (S).

In the example shown, guidewire (904) includes a plurality of navigation sensor assemblies (962*a*, 962*b*) fixedly secured to elongate member (940) that are operable to generate signals that are indicative of the position and orientation of elongate member (940) and/or guidewire tip member (950) within the patient (PA). More particularly, guidewire (904) includes a plurality of (e.g., three) first navigation sensor assemblies (962*a*) and a plurality of (e.g., two) second navigation sensor assemblies (962*b*). First navigation sensor assemblies (962*a*) may each include at least one electromagnetic coil (not shown) operable to generate signals indicative of the position of the respective coil and thereby indicative of the position of a portion of elongate member (940) in three-dimensional space when positioned within an alternating electromagnetic field generated by field generators (20), in a manner similar to that described above. Second navigation sensor assemblies (962*b*) may each include one or more active current location (ACL) electrodes. In some versions, first and second navigation sensor assemblies (962*a*, 962*b*) may be collectively configured as a flexible printed circuit board (PCB). By way of example only, navigation sensor assemblies (962*a*, 962*b*) may be configured and operable in accordance with at least some of the teachings of U.S. patent application Ser. No. 17/584,693, entitled "Flexible Sensor Assembly for ENT Instrument," filed Jan. 26, 2022, the disclosure of which is incorporated by reference herein, in its entirety; and/or U.S. patent application Ser. No. 17/547,517, entitled "Electrical Paths Along Flexible Section of Deflectable Sheath," filed Dec. 10, 2021, the disclosure of which is incorporated by reference herein, in its entirety.

As shown in FIG. 13A, FIG. 13B, FIG. 13C and FIG. 13D, the distal portion of guidewire (904) is configured to assume a variety of poses. For example, the distal portion of guidewire (904) may be configured to assume a generally straight pose (FIG. 13A), such as for facilitating advancement of the distal portion of guidewire (904) through lumens (312, 328) of dilator (302). The distal portion of guidewire (904) may also be configured to assume a generally J-shaped pose (FIG. 13B) in which the distal portion of guidewire (904) bends backwards such that distal tip (954) of guidewire tip member (950) faces proximally. In addition, or alternatively, the distal portion of guidewire (904) may be configured to assume a generally lasso-shaped pose (FIG. 13C) in which the distal portion of guidewire (904) spirals such that distal tip (954) of guidewire (904) faces distally. In some cases, the distal portion of guidewire (904) may be configured to assume a generally undulating pose (FIG. 13D) in which the distal portion of guidewire (904) bends upwardly and downwardly in an alternating manner.

Figures 13A, 13B, 13C, 13D:
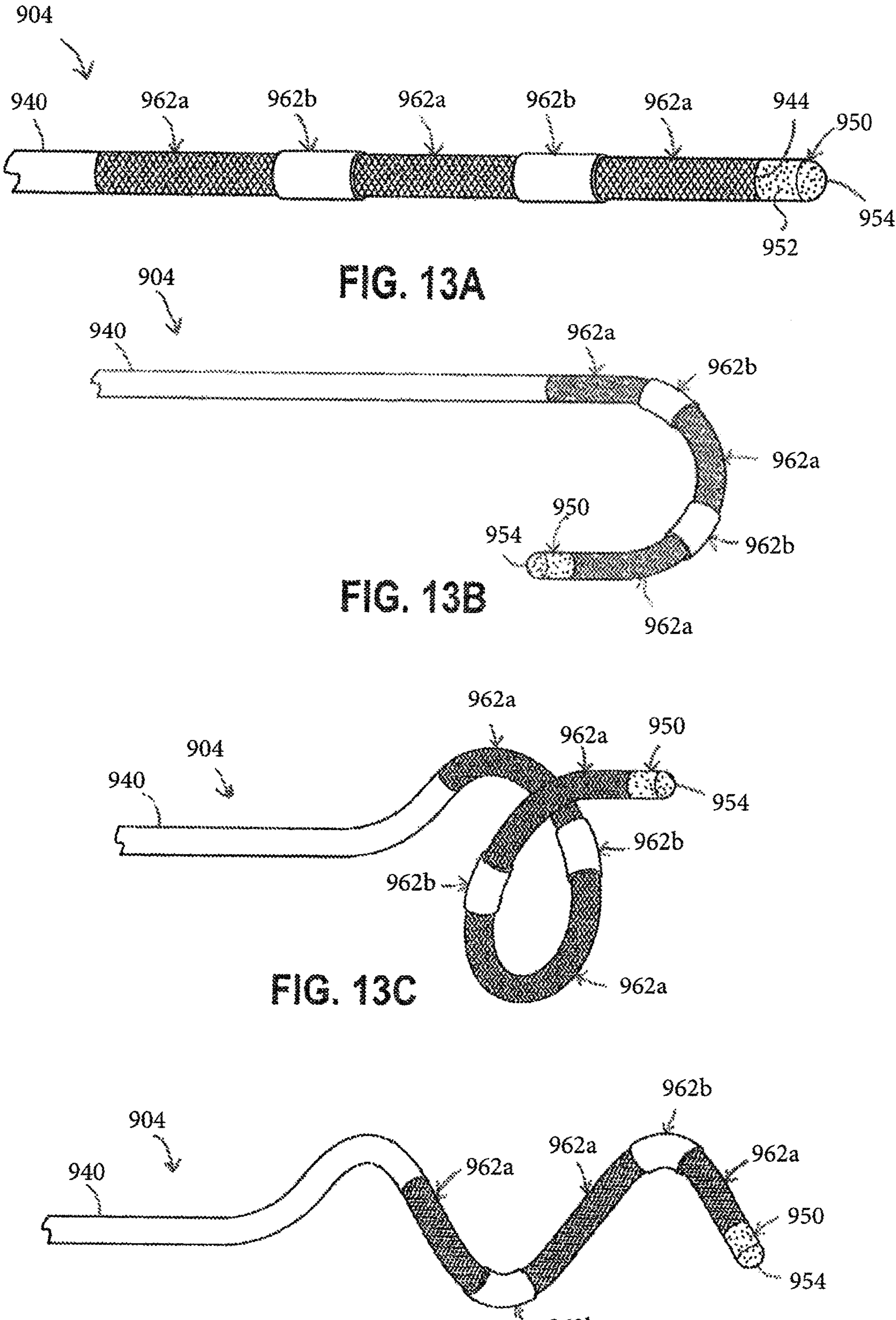
FIG. 13A depicts a side elevational view of a distal portion of another example of a guidewire for use with the transseptal puncture instrument of FIG. 4A and having a distal tip member and a plurality of navigation sensor assemblies, with the guidewire in a straight pose.
FIG. 13B depicts a side elevational view of the distal portion of the guidewire of FIG. 13A, with the guidewire in a J-shaped pose.
FIG. 13C depicts a side elevational view of the distal portion of the guidewire of FIG. 13A, with the guidewire in a lasso-shaped pose.
FIG. 13D depicts a side elevational view of the distal portion of the guidewire of FIG. 13A, with the guidewire in an undulating pose.

The distal portion of guidewire (904) may be configured to transition from the straight pose shown in FIG. 13A to any one or more of the J-shaped pose shown in FIG. 13B, the lasso-shaped pose shown in FIG. 13C, or the undulating pose shown in FIG. 13D, in response to distal tip (954) of guidewire tip member (950) impacting a wall or other structure of the heart (H) that is past the atrial septum (S), such as due to inadvertent over-advancement of guidewire (904) through the opening (O). In this regard, it will be appreciated that such transitioning of guidewire (904) from the straight pose to any of the J-shaped pose, the lasso-shaped pose, or the undulating pose may further reduce the risk of distal tip (954) injuring the wall or other structure of the heart (H) that is past the atrial septum (S). In addition, or alternatively, such transitioning of the distal portion of guidewire (904) may allow the distal portion of guidewire (904) to serve as an anchor in the left atrium such that one or more additional instruments (e.g., catheter of catheter assembly (100), etc.) may be advanced distally over guidewire (904), through the opening (O), and into the left atrium. The position data generated by position related signals received from navigation sensor assemblies (962*a*, 962*b*) may be processed by the processor of console (12) for determining whether the distal portion of guidewire (904) is in the straight, J-shaped, lasso-shaped, or undulating pose, for example, and/or for providing a visual indication to the operator to show the operator where the distal portion of guidewire (904) and/or guidewire tip member (950) is located within the patient (P) in real time.

H. Example of Guidewire with Pair of Coaxial Tip Members

Figure 14:
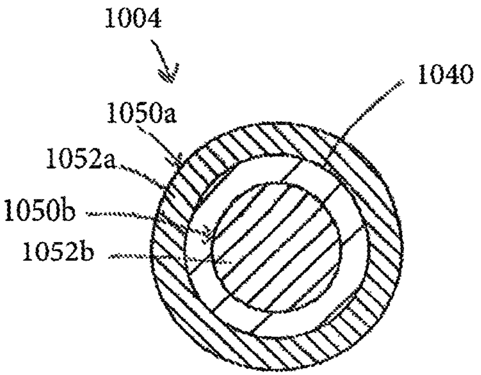
FIG. 14 depicts a cross-sectional end view of another example of a guidewire for use with the electrical instrument of FIG. 4A and having a pair of coaxial distal tip members.

In some instances, it may be desirable to provide a guidewire having a pair of coaxial tip members operable to apply bipolar electrical energy to tissue independently of the dilator. FIG. 14 shows a distal portion of another example of a guidewire (1004) having such a configuration, and which may be incorporated into instrument (300) in place of guidewire (304). Guidewire (1004) may be similar to guidewire (304) described above except as otherwise described below. In this regard, guidewire (1004) of this example includes an elongate member (1040) extending to a distal end (not shown). Elongate member (1040) may include a shaft or a coil, for example. In cases where elongate member (1040) includes a coil, the coil may be wrapped about a core wire (not shown), which may be secured relative to the distal end and prevent the coil from elongating when the coil is placed under tensile stress. Elongate member (1040) is sized for insertion through lumens (312, 328) of dilator (302). Dilator (302) may thus be used to assist in positioning a pair of guidewire tip members (1050*a*, 1050*b*) of guidewire (1004) in relation to a target puncture location of the septum (S). Guidewire tip members (1050*a*, 1050*b*) may be formed of an electrically conductive material, such that each guidewire tip member (1050*a*, 1050*b*) may serve as a monopolar electrode or as a bipolar electrode as described herein.

In the example shown, at least a distal portion of elongate member (1040), such as the portion of elongate member (1040) that is radially between guidewire tip members (1050*a*, 1050*b*), comprises an electrically non-conductive (e.g., insulative) material, such as plastic, to electrically isolate guidewire tip members (1050*a*, 1050*b*) from each other. In this regard, each guidewire tip member (1050*a*, 1050*b*) of the present example includes a body (1052*a*, 1052*b*). Each body (1052*a*, 1052*b*) is fixedly secured to the distal end of elongate member (1040), such that a distal region of each body (1052*a*, 1052*b*) is exposed for contact with tissue. Second guidewire tip member (1050*b*) is received within an interior of elongate member (1040), while first guidewire tip member (1050*a*) is positioned about an exterior of elongate member (1040). As shown, bodies (1052*a*, 1052*b*) each have a circular cross-sectional shape that are coaxial with each other.

Guidewire tip members (1050*a*, 1050*b*) may each be electrically coupled with electrical generator (306) via respective wires (not shown) extending along elongate member (1040), such that guidewire tip members (1050*a*, 1050*b*) may thereby be operable to apply bipolar electrical energy to the tissue of the septum (S), with one guidewire tip member (1050*a*, 1050*b*) serving as an active electrode and the other guidewire tip member (1050*a*, 1050*b*) serving as a return electrode to ablate the tissue, for example. In this manner, guidewire (1004) may be capable of forming the opening (O) independently of dilator (302), such that dilator tip member (320) may be omitted.

I. Example of Guidewire with Proximal and Distal Electrodes

Figure 15:
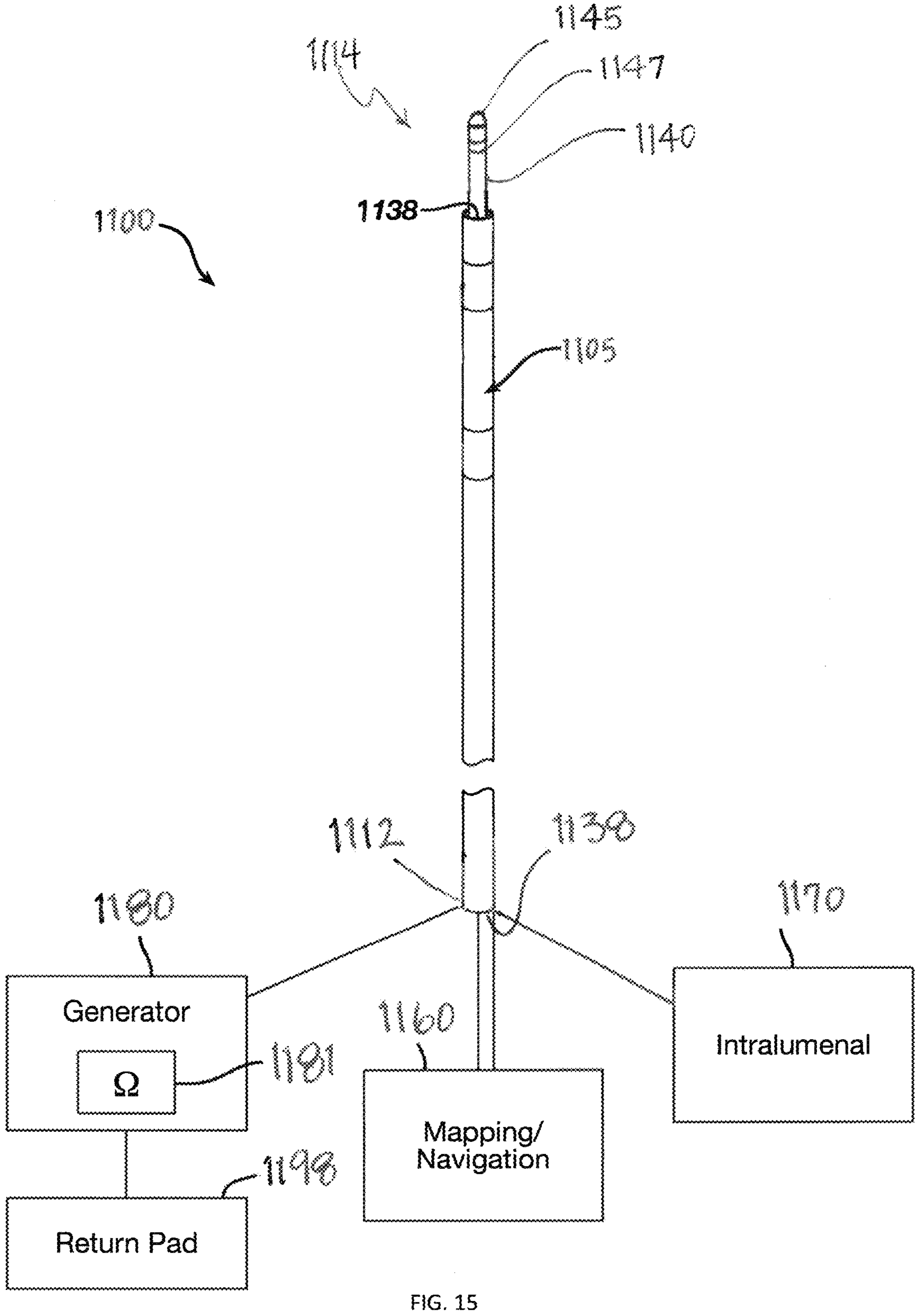
FIG. 15 shows an example transseptal puncturing system including an example of an atraumatic needle instrument with a first electrode configured for ablation and a second electrode configured for impedance measurement.

In some instances, [need to edit this] it may be desirable to provide a needle instrument, for example, a guidewire, having an electrically-conductive distal to ablate tissue with a nonablating electrode operable to provide impedance signals to determine (i) whether the distal end of needle instrument is inside the guiding sheath or outside exposed to blood, (ii) if the distal end of the needle instrument has crossed the septum tissue; and (iii) location and direction of needle instrument. FIG. 15 shows an example of a transseptal puncturing system 1100 that includes a lumened instrument or guiding sheath (1105), a needle instrument 1114, an electrical energy generator 1180, a return pad (e.g., body patch) (1198), a mapping/navigation module 1160, and an intralumental module 1170. As a guidewire, the needle instrument (1114) may be similar to guidewire (304) described above except as otherwise described below. The needle instrument (1114) of this example includes an elongate member (1140) with an electrically-conductive distal end or electrode (1145) operable to be electrically energized by the electrical generator (1180) for ablating septum tissue. Elongate member (1140) may include a shaft or a coil, for example. In cases where elongate member (1140) includes a coil, the coil may be wrapped about a core wire (not shown), which may be secured relative to the distal end and prevent the coil from elongating when the coil is placed under tensile stress. Elongate member (1140) is sized for insertion through lumen (1138) of a lumened instrument, for example, the guiding sheath (1105). The sheath (1105) may thus be used to assist in positioning the distal end (1145) of the needle instrument (1114) in relation to a target puncture location of the septum (S). The distal electrode (1145) may be formed of an electrically conductive material, such that it may serve as a monopolar electrode or as a bipolar electrode as described herein. The distal electrode (1145) may be formed as a dome tip electrode or as a distal ring electrode, as known in the art. It is understood that while the instrument is referred to herein as a needle instrument the instrument has an atraumatic distal end, that is without any tissue-piercing distal end that has a sharp or pointed configuration. That is, without ablation, the needle instrument is not intended to pierce or puncture tissue merely due to its physical structure, and thus the distal end may be hemispherical, flat, domed or of any other suitable configuration or profile.

The distal electrode (1145) is electrically connected to receive electrical energy from the electrical generator (1180) via at least an electrically conductive wire extending along elongate member (1140) or any other suitable electrically conductive element(s), such as via one or more electrically conductive traces (e.g., of a flex circuit, etc.) extending along elongate member (1140) or one or more other electrical conductors embedded directly into the elongate member (1140). Distal electrode (1145) is thus operable to apply electrical energy to the tissue of the septum (S) to form the opening (O) as described herein.

The needle instrument (1114) advantageously includes a second electrode (1147) electrically insulated from the ablation distal electrode (1145). For example, the needle instrument (1114) includes a proximal electrode (1147) proximal of the distal electrode (1145), for example, configured as a ring electrode. In the example shown, at least a portion of elongate member (1140) spans between the distal electrode (1145) and the proximal electrode (1147) comprises an electrically non-conductive (e.g., insulative) material, such as plastic, to electrically isolate the distal electrode (1145) and the proximal electrode (1147) from each other.

In some embodiments, the generator (1180) includes an impedance monitoring module (1181) that is configured to measure impedance, including impedance at the proximal or second nonablating electrode (1147) of the needle instrument (1114). The generator (1180) can be configured to provide electrical energy to the distal electrode (1145) based at least in part on the impedance measured by the impedance monitoring module (1181) at the proximal or second nonablating electrode (1147) in determining position of the needle instrument in stages of a transseptal puncture procedure, including approach, contact, penetration and passage through the septum, and to suspend application of electrical energy to the ablating distal electrode (1145) when at least the distal electrode has passed through the septum.

The mapping/navigation module 1160 can be in electrical contact with location sensor(s) on the guiding sheath (1105) and/or the needle instrument (1114). The navigation module (1160) can be configured to determine a position and/or orientation of the distal portion of the guiding sheath and/or the needle instrument based at least in part on electrical signals from the location sensor(s). The navigation module (1160) can include an electric tracking sub-system and/or a magnetic position tracking sub-system which can function alone or in a hybrid mode as described in U.S. Pat. No. 8,456,182 incorporated herein by reference or as otherwise understood by a person skilled in the pertinent art. The navigation module (1160) can further be in electrical contact with proximal end 1112 of the needle instrument (1114) and can utilize the distal end (1145) of the needle instrument (1114) as a reference electrode for the location sensor(s).

The intralumenal module (1170) can be in communication with a lumen (1138) of the guiding sheath (1105). The intralumenal module (1170) can be configured to perform intralumenal steps as understood by a person skilled in the pertinent art such as sensing pressure and/or providing fluids via the lumen (1138).

Figure 16:
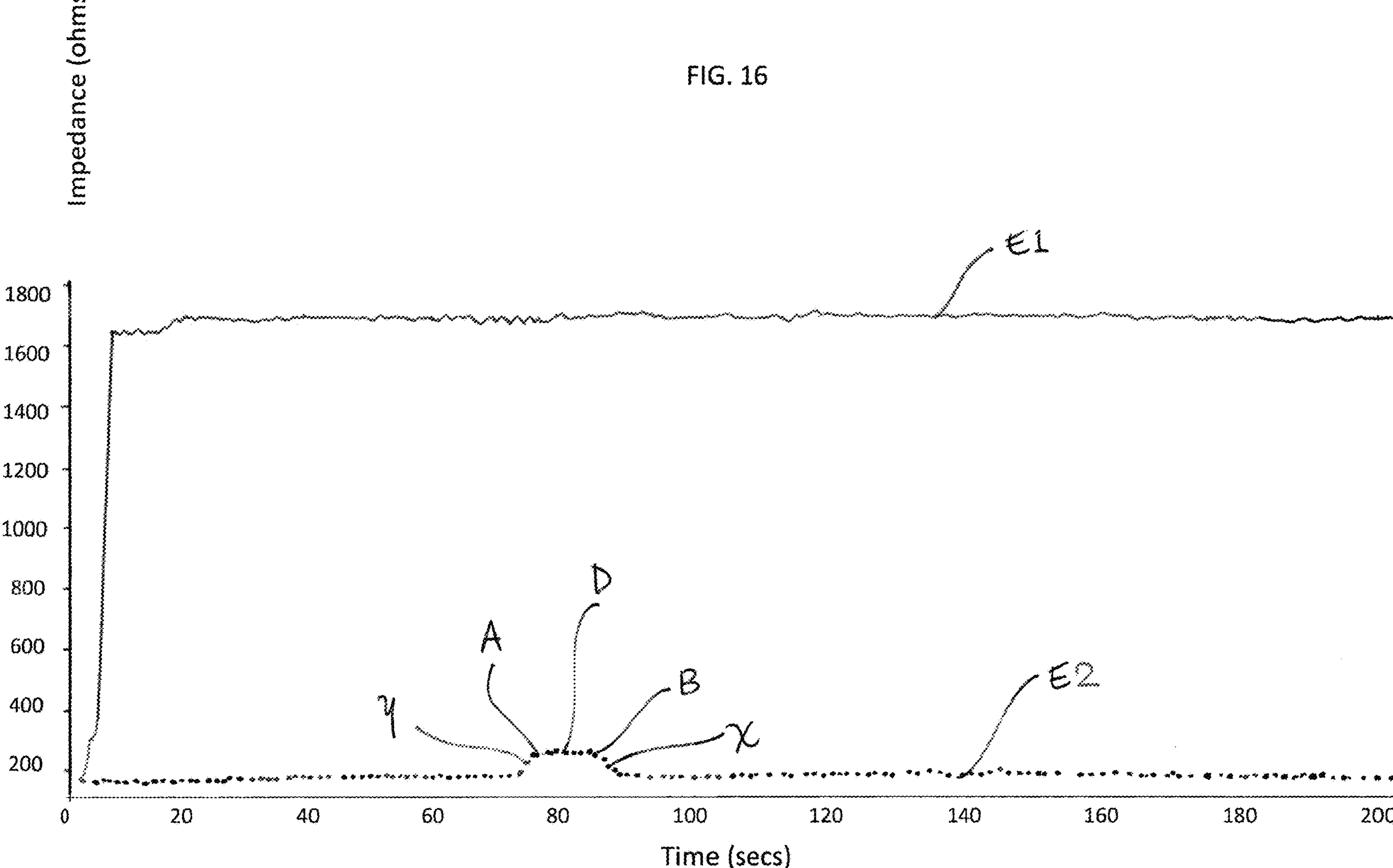
FIG. 16 is a graph of impedance measured at the first and second electrodes during ablation by the first electrode of the needle instrument of FIG. 15 during a transseptal puncture procedure.
Figures 17A, 17B, 17C, 17D, 17E:
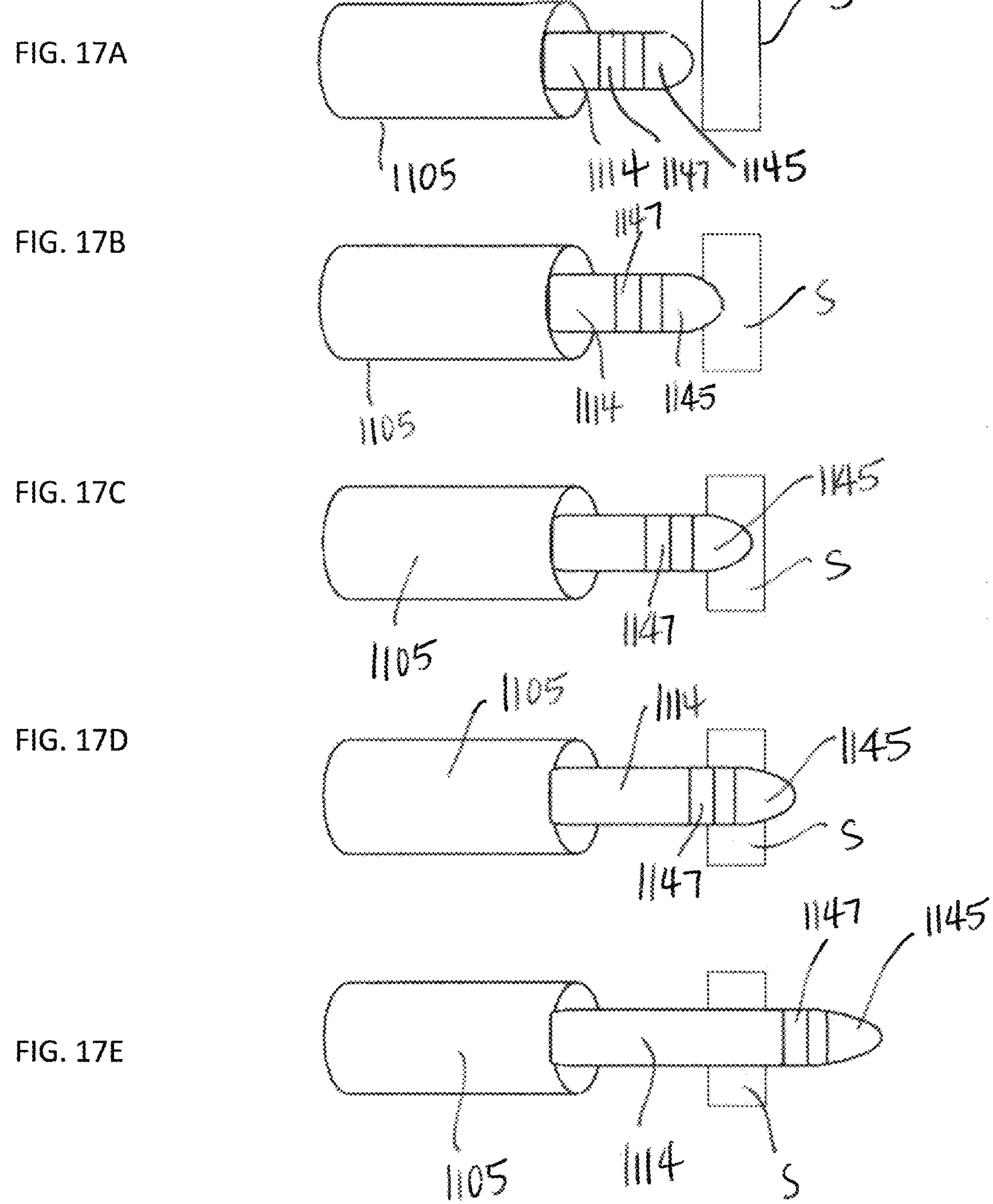
FIG. 17A shows a distal portion of an example of a needle instrument advanced distally past a sheath, with both distal electrode and proximal electrode are exposed to blood outside of the sheath.
FIG. 17B shows the distal portion of FIG. 17A, with distal electrode in tissue contact.
FIG. 17C shows the distal portion of FIG. 17A, with distal electrode ablating and penetrating the septum S.
FIG. 17D shows the distal portion of FIG. 17A, with distal electrode ablating and further penetrating the septum S and the proximal electrode also in contact with the septum S.
FIG. 17E shows the distal portion of FIG. 17A, with both distal electrode and proximal electrode completing puncture and distally past the septum.

As shown in FIG. 16, a graph illustrates an example of measured impedance E1 over time at the electrically-conductive distal electrode (1145) (solid line) and measured impedance measured E2 at the proximal electrode (1147) (broken lines) of the needle instrument (1114). With reference to FIG. 17A, at time zero, the needle instrument (1114) has been advanced distally past the sheath (1105) such that both the distal electrode (1145) and the proximal electrode (1147) are exposed to blood outside of the sheath and each of the measured impedances E1 and E2 is about 300 ohms.

With reference to FIG. 17B, at about 3.0 secs, the needle instrument (1114) is further advanced and the distal electrode (1145) contacts the septum S. The measured impedance E1 at the distal electrode (1145) increases slightly to about 350 ohms, whereas the measured impedance E2 at the proximal electrode (1147) remains at about 300 ohms.

With reference to FIG. 17C, at about 8.0 secs, the distal electrode (1145) is energized to ablate the septum S and begins to penetrate the septum S. The measured impedance E1 at the distal electrode (1145) increases significantly to about 2000 ohms, whereas the measured impedance E2 at the proximal electrode (1147) remains at about 300 ohm (or about one-tenth of the measured impedance E1).

With reference to FIG. 17D, at about 75 secs, the needle instrument (1114) is further advanced and the distal electrode (1145) remains in contact with and continues to be energized to ablate the septum S and the proximal electrode (1147) also comes into contact with the septum S. The measured impedance E1 at the distal electrode (1145) remains at about 2000 ohms and the measured impedance E2 at the proximal electrode (1147) increases to about 350 ohms.

With reference to FIG. 17E, at about 90 seconds, the needle instrument (1114) while still energized is further advanced and the both the distal electrode (1145) and the proximal electrode (1147) are moved distally past the septum S. The measured impedance E1 at the distal end (1145) remains at 2000 ohms with noise, whereas the measured impedance E2 at the proximal electrode (1147) decreases and returns to about 300 ohms.

As clearly depicted in the graph of FIG. 16, the measured impedance E1 at the ablating distal electrode (1145) includes significant "noise". In contrast, the measured impedance E2 at the proximal electrode (1147) is generally "noise-free", such that the graph provides a more readily detectable or measurable, if not obvious, demarcation D including a clear increase A followed by a clear decrease B in the measured impedance E2 at the proximal electrode (1147) in the duration between about 75-90 secs when the proximal electrode (1147) makes initial contact with septum tissue and until tissue contact ceases when the proximal electrode (1147) passes through the septum tissue. Advantageously, upon detection of an event such as, for example, this demarcation in the measured impedance E2 of the proximal electrode (1147), including a decrease X subsequent to an initial increase Y, the application of energization to the ablation electrode (1145) from the electrical generator (1180) can be immediately ceased on the presumption that the proximal electrode (1147) has been advanced distally past the septum S, so as to minimize possible injury to tissue in the left atrium due to excessive advancement of the needle instrument into the left atrium.

Figure 18:
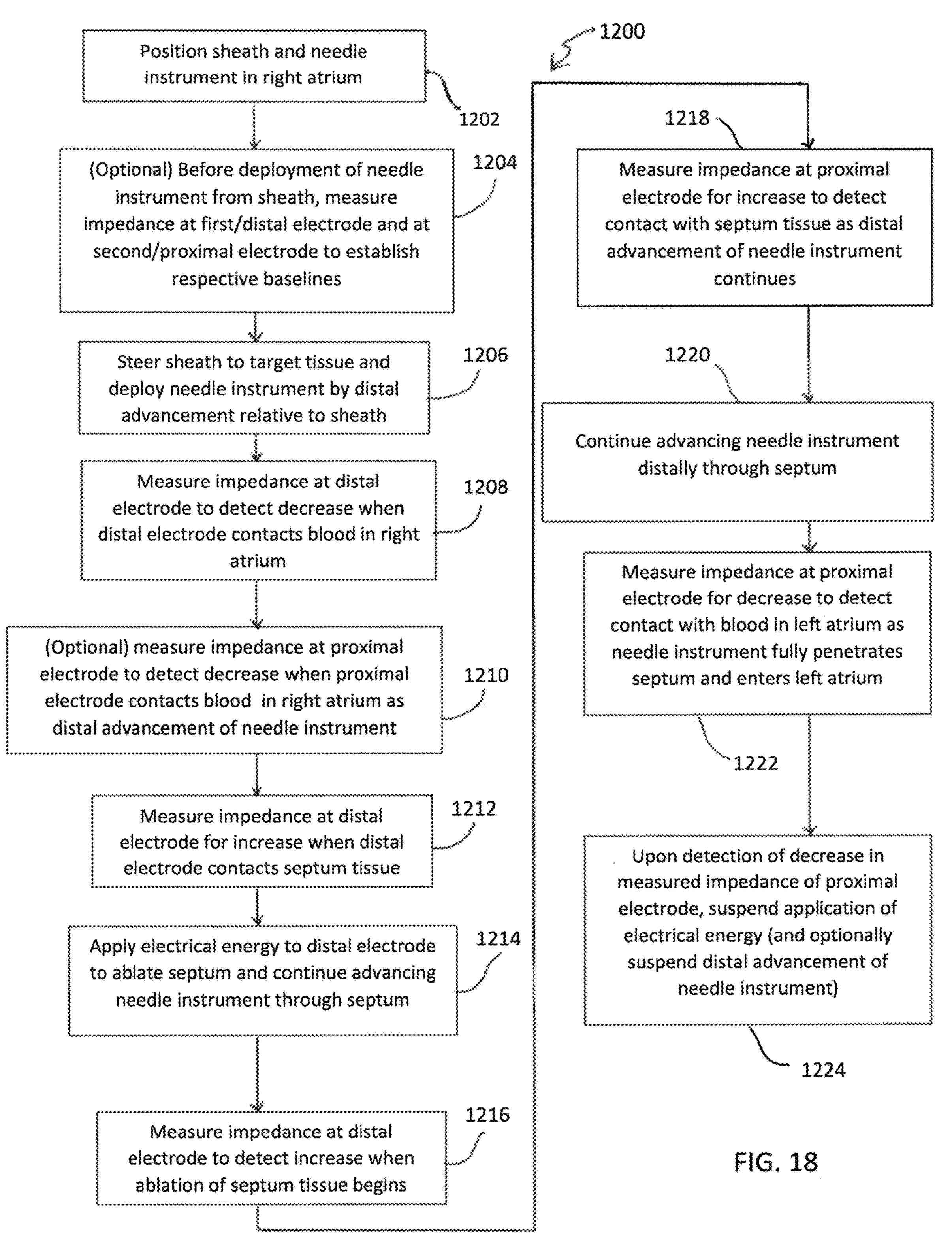
FIG. 18 is a flow diagram outlining steps of an example method for transseptal puncture according to aspects of the present invention.

FIG. 18 is a flow diagram outlining steps of an example method 1200 for transseptal puncture. At step 1202, the sheath (1105) and the needle instrument (1114) are positioned in a right atrium RA.

At step 1204, as an option, before deployment of the needle instrument (1114) from the distal end of the sheath (1105), impedance measurements can be taken at both a first or distal electrode (1145) and a second or proximal electrode (1147) to establish respective baselines or initial impedances $E1_0$ and $E2_0$ of the electrodes prior to being exposed to blood.

At step 1206, for example, using a location sensor provided on either the sheath (1105) or the needle instrument (1114) with location signals received by the navigation module of the first driver module (14) of the console (12), the distal end of the sheath is steered to thereby steer the distal electrode (1145) to the target tissue.

At step 1208, exposure of only the distal electrode (1145) to blood in the right atrium can be determined based at least in part on measuring the impedance E1 at the distal electrode (1145), including measuring a decrease from the baseline impedance $E1_0$. At step 1210, as an option, exposure of the proximal electrode (1147) to blood in the right atrium can be determined based at least in part on measuring the impedance E2 at the proximal electrode (1147), including a decrease from the baseline impedance $E2_0$.

At step 1212, septum tissue contact by the distal electrode (1145) can be determined based at least in part on measuring the impedance E1 at the distal electrode, including measuring an increase in the impedance E1.

At step 1214, upon or after measuring the increase in step 1212, electrical energy is applied by the electrical generator (1180) to the electrically-conductive distal electrode (1145) of the needle instrument (1114) to initiate ablation and penetration of the target tissue, as distal advancement of the needle instrument (1114) into the septum continues.

At step 1216, ablation and initial penetration of the distal electrode (1145) can be determined based at least in part on measuring the impedance E1 at the distal electrode (1145), including measuring a significant increase.

At step 1218, contact between the proximal electrode E2 and the septum can be detected based at least in part on measuring the impedance E2 at the proximal electrode (1147), including measuring an increase marking a start of the demarcation D of the graph of FIG. 16.

At step 1220, electrical energy continues to be applied to the distal electrode (1145) as the distal electrode further ablates septum tissue and continues to pass through the septum S.

Notably, where the separation distance between the distal electrode and the proximal electrode is predetermined and known, the position (absolute or relative) of one electrode can be determined by the position of the other.

At step 1222, full puncture of and passage through the septum and entry into the left atrium by both the distal electrode (1145) and the proximal electrode (1147) can be determined based at least in part on measuring the impedance E2 at the proximal electrode (1147), including measuring a decrease indicating that the proximal electrode has encountered blood in the left atrium. It is understood that the distal electrode (1145) may also exhibit a decrease in measured impedance; however, the decrease may be overshadowed by the high and noisy impedance at the distal electrode if electrical energy is still being applied to the distal electrode (1145).

At step 1224, upon determining the entry of the proximal electrode (1147) into the left atrium, application of electrical energy to the distal electrode by the electrical generator (306) can be suspended and optionally distal advancement of the needle instrument can also be suspended.

It is understood that other embodiments of the method of the present invention need not include each of the blocks of the flow diagram of FIG. 18. For example, one embodiment may exclude one or more of Blocks 1204, 1208, 1210, 1212 and 1216.

Impedances measured by the impedance monitoring module may include (i) pre-contact impedances, such as impedances measured at the distal electrode and the proximal electrode prior to contact with the septum, (ii) tissue impedances, such as impedances measured at the distal electrode and the proximal electrode when these electrodes come into contact with the septum, and (iii) post-penetration impedances, such as impedances measured at the distal electrode and proximal electrode after penetration of the septum.

Moreover, based on a comparison of different permutations of measured impedances E1 and E2, for example, relative to each other and of measured impedance E2 to a predetermined threshold impedance HIT, assessments can be made as to location of the first/distal electrode (1145) and the second/proximal electrode (1147) relative to the septum S, as illustrated in FIG. 19A, FIG. 19B, FIG. 19C, FIG. 19D and FIG. 19E. In some embodiments, the predetermined threshold impedance HIT is the impedance of septum tissue which is generally greater than the impedance of blood.

Figures 19A, 19B, 19C, 19D, 19E:
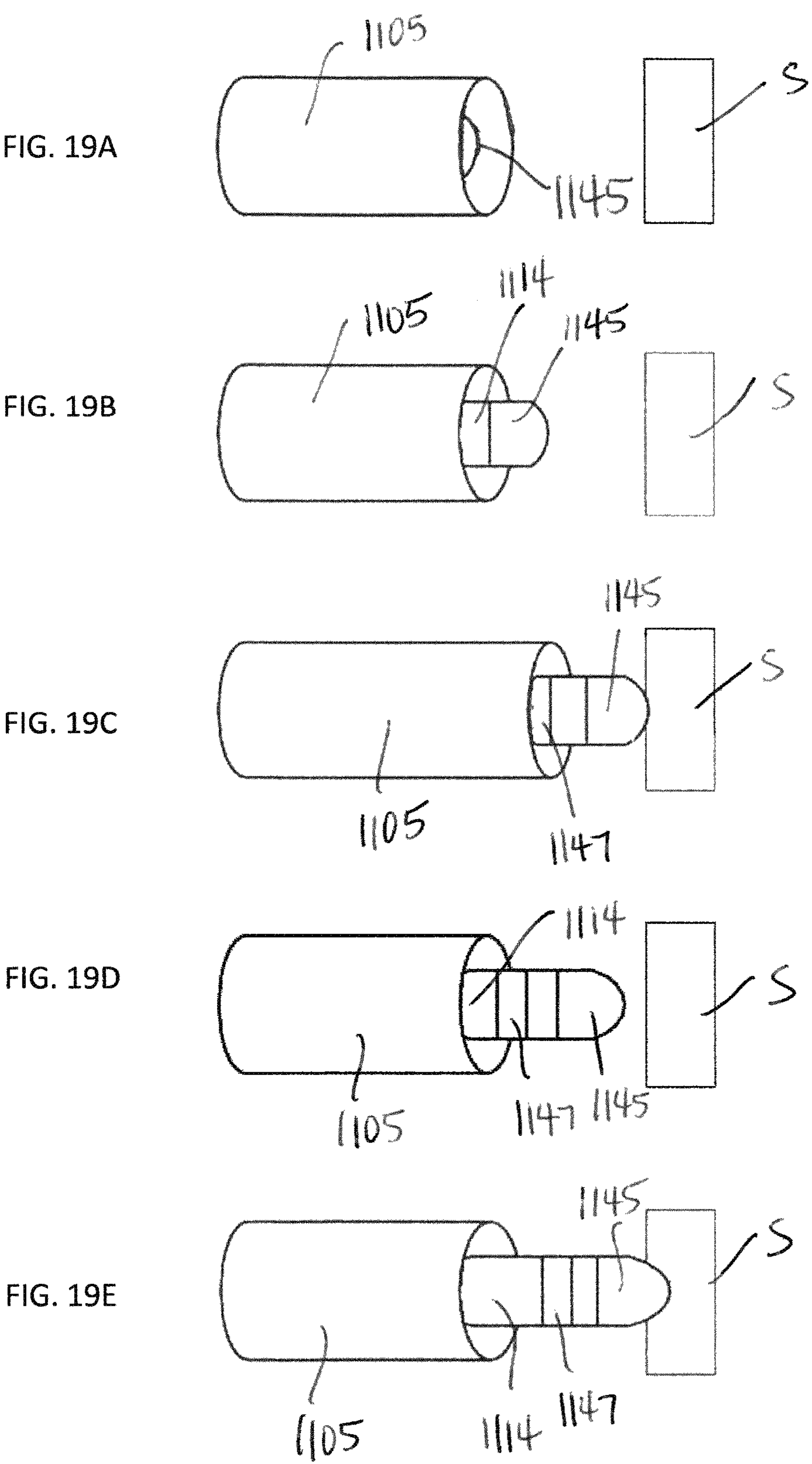
FIG. 19A depicts an atraumatic needle instrument prior to deployment from a guiding sheath.
FIG. 19B depicts the atraumatic needle instrument distally advanced relative to the guiding sheath, with a distal electrode exposed to blood but without tissue contact.
FIG. 19C depicts the guiding sheath distally advanced, with the distal electrode in contact with septum tissue but proximal electrode remaining inside the sheath.
FIG. 19D depicts the atraumatic needle instrument distally advanced relative to the guiding sheath, with both distal electrode and proximal electrode exposed to blood but without tissue contact
FIG. 19E depicts the atraumatic needle instrument advanced relative to the guiding sheath, with the distal electrode in tissue contact and ready to be energized for ablation and the proximal electrode exposed to blood but without tissue contact.

FIG. 19A depicts the needle instrument (1114) with both the distal and proximal electrodes (1145, 1147) still within the sheath (1105) and not exposed to blood, where each of the measured impedances E1 and E2 is greater than the predetermined threshold impedance HIT. Additionally, each measured impedances E1 and E2 may be generally equal to each other.

FIG. 19B depicts the needle instrument (1114) having been advanced relative to the sheath (1105) such that only the distal electrode (1145) is distal of a distal end of the sheath and exposed to blood but without tissue contact, where the measured impedance E1 is less than the predetermined threshold impedance HIT but the measured impedance E2 remains greater than the predetermined threshold impedance HIT.

FIG. 19C depicts the sheath (1105) having been advanced such that the distal electrode (1145) is in contact with the septum S but the proximal electrode (1147) remains inside the sheath and not exposed to blood, where the measured impedance E2 remains greater than the predetermined threshold impedance HIT. Additionally, the measured impedance E1 increases due the transition from contact with blood to contact with septum tissue. With the distal electrode in contact with the septum, the measured impedance E1 at the distal electrode may generally equal the predetermined threshold impedance HIT and may also remain less than the measured impedance E2.

FIG. 19D depicts the needle instrument (1114) having been advanced relative to the sheath (1105) such that both the distal electrode (1145) and the proximal electrode (1147) are distal of the distal end of the sheath and exposed to blood but without tissue contact, where both of the measured impedances E1 and E2 are less than the predetermined threshold impedance HIT.

FIG. 19E depicts the needle instrument (1114) having been advanced relative to the sheath such that the distal electrode (1145) is in tissue contact and energized for ablation and the proximal electrode (1147) is distal of the distal end of the sheath and exposed to blood in the right atrium, where the measured impedance E1 is greater than the predetermined threshold impedance HIT if ablation has commenced, and the measured impedance E2 is less than the predetermined threshold impedance HIT.

It is understood that the first (or ablation) electrode (1145) and the second (or impedance) electrode (1147) may be located at any suitable locations on the needle instrument (1114). They can be at different longitudinal locations with either one being more proximal (or more distal) than the other, or they can be at generally the same longitudinal location, provided the two electrodes are electrically isolated from each other such that noise affecting the ablation electrode (1145) during energization minimally impacts the second electrode (1147).

FIG. 20 is a flow diagram 1300 outlining steps of an example method for determining relative position of first and second electrodes of a needle instrument relative to a septum. Beginning at Start 1302, the method proceeds to Query 1304 which compares measured impedance E1 at the first/distal electrode (1145) to the predetermined threshold impedance HIT. If measured impedance E1 is not greater than the predetermined threshold impedance HIT, the method proceeds to Query 1306 which compares if the measured impedance E1 is equal to the predetermined threshold impedance HIT. If yes, the method proceeds to Query 1314 which compares the measured impedance E2 at the second/proximal electrode (1147) with the predetermined threshold impedance HIT. If the measured impedance E2 at the proximal electrode (1114) is less than the predetermined threshold impedance HIT, the method proceeds to Block 1318 which indicates that the needle instrument (1114) is positioned relative to the sheath (1105) and the septum S as shown in FIG. 19E. If no, the method proceeds to Block 1322 which indicates that the needle instrument (1114) is positioned relative to the sheath (1105) and the septum S as shown in FIG. 19C.

If at Query 1306 the measured impedance E1 of the distal electrode (1145) is equal to the predetermined threshold impedance HIT, the method proceeds to Query 1310 which compares measured impedance E2 to the predetermined threshold impedance HIT. If the measured impedance E2 of the proximal electrode (1147) is greater than the predetermined threshold impedance HIT, the method proceeds to Block 1316 which indicates that the needle instrument is positioned relative to the sheath (1105) and the septum S as shown in FIG. 19B. If at Query 1310 the measured impedance E2 is not greater than the predetermined threshold impedance HIT, the method proceeds to Block 1320 which indicates that the needle instrument is positioned relative to the sheath (1105) and the septum S as shown in FIG. 19D.

If at Query 1320, the measured impedance E1 of the distal electrode (1145) is greater than the predetermined threshold impedance HIT, then the method proceeds to Query 1308 which compares the measured impedance E2 of the proximal electrode (1147) to the predetermined threshold impedance HIT. If the measured impedance E2 is greater than the predetermined threshold impedance HIT, then the method proceeds to Block 1312 which indicates that the needle instrument is positioned relative to the sheath (1105) and the septum S as shown in FIG. 19A. If the measured impedance E2 is not greater than the predetermined threshold impedance HIT, the method proceeds to Query 1306.

Upon the method reaching Block 1316, 1320, 1324, 1318 or 1312, the method proceeds to End 1324.

Notably, the proximal electrode (1147) can provide needle instrument direction visualization using an advanced current localization (ACL) tracker module of the navigation module of the first driver module (14). As an electrical tracking system that is based on impedance, the ACL tracker module can deliver current to the proximal electrode (1147) from the electrical generator (306), where the current spreads from the proximal electrode (1147) through the body of the patient to body patches affixed to the skin of the patient's body, and location of the proximal electrode is determined based on current distribution at the body patches. Methods for impedance-based position sensing are disclosed, for example, in U.S. Pat. No. 5,983,126 to Wittkampf, in U.S. Pat. No. 6,456,864 to Swanson, and in U.S. Pat. No. 5,944,022 to Nardella, all of whose disclosures are incorporated herein by reference. Hybrid position sensing systems and methods which combine magnetic and electrical position sensing techniques are disclosed, for example, in U.S. Patent Publication No. 2007/0016007 to Govari. In these systems, a magnetic position sensor provides an accurate position reference for calibrating less accurate, electrical impedance-based measurements. For this purpose, a hybrid probe, such as an EP instrument or catheter, comprising a triaxial magnetic position sensor and one or more electrodes is used to correlate the magnetic position measurements with the impedance-based measurements. Systems of this sort alleviate the need for multiple magnetic position sensors, and thus benefit from both magnetic position sensing and impedance-based sensing.

A hybrid EP catheter is positioned in a body cavity, such as a heart chamber. Externally-applied magnetic fields are measured by the magnetic field sensor, and accurate position coordinates of the catheter are derived. Currents of voltages from body-surface electrodes are also applied, and impedances between the body-surface electrodes and the catheter electrodes are measured. The dual position measurements are repeated at multiple locations within the body cavity in order to generate a calibration map, correlating the impedance measurements with position coordinates ascertained by the magnetic field sensor. Subsequently, additional instruments having diagnostic or therapeutic functions may be introduced into the body cavity. The additional instruments may be introduced simultaneously with the hybrid catheter and/or following removal of the hybrid catheter from the body. These additional catheters also incorporate electrodes similar to those of the hybrid catheter but need not to include magnetic field sensors. Impedance measurements taken from the electrodes on the additional instruments are correlated with the calibration map in order to determine accurate position coordinates of these additional instruments.

Both magnetic and impedance-based measurements are taken while the hybrid EP catheter is held steady, in a known configuration. In this configuration, the position of each electrode is known a priori relative to the magnetic sensor. Positions of the electrodes are therefore known on the basis of the magnetic position measurements, and the known positions may be used to calibrate impedance measurements taken at each electrode.

With the needle instrument (1114) carrying the proximal electrode (1147), impedance measured at the proximal electrode can be used by the ACL tracker module to provide position and orientation of the distal end of the needle instrument, including position and orientation relative to the septum and whether the distal end of the needle instrument is in contact with the septum and whether the distal end has penetrated and fully passed through the septum in entering the left atrium.

V. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body assembly; (b) a shaft extending distally from the body assembly, the shaft including a distal end; and (c) at least one tip member secured at the distal end of the shaft, the at least one tip member and the distal end of the shaft being sized and configured to fit within a chamber of a heart of a human subject, the at least one tip member including: (i) an atraumatic distal tip, the atraumatic distal tip being configured to deliver electrical energy to tissue for forming an opening through the tissue, and (ii) an exterior dilation surface adjacent to the atraumatic distal tip, the exterior dilation surface being configured to enlarge the opening formed by the atraumatic distal tip.

Example 2

The apparatus of Example 1, the atraumatic distal tip and the exterior dilation surface together defining a dome shape.

Example 3

The apparatus of any of Examples 1 through 2, the exterior dilation surface being at least one of curved or tapered radially inwardly toward the atraumatic distal tip.

Example 4

The apparatus of any of Examples 1 through 3, the at least one tip member being positioned on a single angular side of the distal end of the shaft.

Example 5

The apparatus of any of Examples 1 through 4, the at least one tip member including at least two tip members, the at least two tip members being operable to cooperate with each other to deliver bipolar electrical energy to the tissue.

Example 6

The apparatus of Example 5, the at least two tip members being positioned adjacent to each other on respective angular sides of the distal end of the shaft.

Example 7

The apparatus of Example 5, the at least two tip members being positioned coaxially with each other.

Example 8

The apparatus of any of Examples 1 through 7, further comprising at least one navigation sensor assembly, the at least one navigation sensor assembly being secured to the shaft.

Example 9

The apparatus of Example 8, the at least one navigation sensor assembly including at least one of an electromagnetic coil or an active current location electrode.

Example 10

The apparatus of Example 8, the at least one navigation sensor assembly including at least one flexible printed circuit board.

Example 11

The apparatus of any of Examples 1 through 10, the shaft further including a first lumen, the first lumen being configured to slidably receive a guidewire.

Example 12

The apparatus of Example 11, the at least one tip member including a second lumen coaxial with the first lumen, the second lumen being configured to slidably receive the guidewire.

Example 13

The apparatus of any of Examples 11 through 12, the at least one tip member being electrically isolated from the first lumen.

Example 14

An instrument comprising: (a) the apparatus of any of Examples 11 through 13; and (b) a guidewire slidably received within the first lumen.

Example 15

The instrument of Example 14, the guidewire being operable to cooperate with the at least one tip member to deliver bipolar electrical energy to the tissue.

Example 16

An apparatus, comprising: (a) an elongate member configured to direct a medical device distally therealong, the elongate member including a distal end; and (b) at least one tip member secured at the distal end of the elongate member, the at least one tip member and the distal end of the elongate member being sized and configured to fit within a chamber of a heart of a human subject, the at least one tip member including an atraumatic distal tip, the atraumatic distal tip being configured to form an opening through a tissue wall, the atraumatic distal tip including at least one electrode operable to deliver electrical energy to the tissue wall as the atraumatic distal tip forms an opening through the tissue wall.

Example 17

The apparatus of Example 16, the at least one tip member including at least two tip members positioned coaxially with each other, the at least two tip members being operable to cooperate with each other to deliver bipolar electrical energy to the tissue.

Example 18

The apparatus of any of Examples 16 through 17, further comprising at least one navigation sensor assembly, the at least one navigation sensor assembly being secured to the elongate member at or near the distal end.

Example 19

An assembly comprising: (a) the apparatus of any of Examples 16 through 18; and (b) a dilator, the dilator including: (i) a lumen, the apparatus being slidably received within the lumen, and (ii) an exterior dilation surface, the exterior dilation surface being configured to enlarge the opening.

Example 20

The assembly of Example 19, the apparatus forming a guidewire.

Example 21

The assembly of any of Examples 19 through 20, the dilator further including at least one electrode, the at least one electrode of the dilator being configured to cooperate with the at least electrode of the atraumatic distal tip to apply bipolar electrical energy to the tissue wall.

Example 22

An apparatus, comprising: (a) a transseptal puncture apparatus, the transseptal puncture apparatus including: (i) an elongate member including a distal end, and (ii) at least one tip member secured at the distal end of the elongate member, the at least one tip member and the distal end of the elongate member being sized and configured to fit within a chamber of a heart of a human subject, the at least one tip member including an atraumatic distal tip, and (b) a dilator, the dilator including: (i) a body assembly, (ii) a shaft extending distally from the body assembly, the shaft including: (A) a distal end, and (B) a lumen, the transseptal puncture apparatus being slidably received within the lumen, and (iii) at least one dilator tip member secured at the distal end of the shaft, the at least one dilator tip member and the distal end of the shaft being sized and configured to fit within the chamber, the at least one tip member including: (A) an atraumatic distal dilator tip, the atraumatic distal dilator tip being operable to cooper with the atraumatic distal tip to deliver bipolar electrical energy to tissue for forming an opening through the tissue, and (B) an exterior dilation surface adjacent to the atraumatic distal dilator tip, the exterior dilation surface being configured to enlarge the opening.

Example 23

The apparatus of Example 22, further including one or more navigation sensors, each navigation sensor of the one or more navigation sensors being configured to generate a signal indicating a real-time position of the navigation sensor in three-dimensional space.

Example 24

The apparatus of Example 23, the one or more navigation sensors including a navigation sensor positioned at or near the distal end of the transseptal puncture apparatus.

Example 25

The apparatus of any of Examples 23 through 24, the one or more navigation sensors including a navigation sensor positioned at or near the distal end of the shaft of the dilator.

Example 26

A method, comprising: (a) inserting an elongate member into a chamber of a heart of a patient, the elongate member having a distal end; (b) engaging the distal end of the elongate member against a septal wall of the heart; (c) forming an opening through the septal wall of the heart, the forming the opening through the septal wall of the heart including applying electrical energy to the septal wall of the heart via the distal end; and (d) enlarging the formed opening through the septal wall of the heart, the enlarging the formed opening through the septal wall of the heart including bearing against the septal wall with a dilation surface.

Example 27

The method of Example 26, the elongate member including a dilator.

Example 28

The method of any of Examples 26 through 27, the elongate member including a guidewire.

Example 29

The method of any of Examples 26 through 28, the distal end having a dome shape.

Example 30

The method of any of Examples 26 through 29, the distal end having a taper defining the dilation surface.

Example 31

The method of any of Examples 26 through 30, the distal end including a first electrode, the applying electrical energy to the septal wall of the heart via the distal end including applying electrical energy via the first electrode.

Example 32

The method of Example 31, the distal end including a second electrode, the applying electrical energy to the septal wall of the heart via the distal end including applying bipolar electrical energy via the first and second electrodes.

Example 33

The method of any of Examples 31 through 32, the elongate member having a guidewire slidably disposed within the elongate member, the method further comprising engaging a distal end of the guidewire against the septal wall of the heart while engaging the distal end of the elongate member against the septal wall of the heart.

Example 34

The method of Example 33, the distal end of the guidewire including a second electrode, the second electrode, the applying electrical energy to the septal wall of the heart via the distal end including applying bipolar electrical energy via the first and second electrodes.

Example 35

The method of any of Examples 26 through 34, further comprising tracking a real-time position of the distal end of the elongate member via one or more navigation sensors.

VI. Miscellaneous

It should be understood that various modes of energized atraumatic transseptal puncture are possible, including but not limited to RF and IRE (including monopolar or bio-polar high-voltage DC pulses) or combinations may be used depending on need, availability/and/or preference. Accordingly, references herein to “energy” and “generators” herein shall be understood to encompass all such modalities with the scope being determined by the claims herein.

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A transseptal puncture system, comprising:
- a guiding instrument configured with a lumen;
- an elongated instrument configured to move longitudinally within the lumen, the elongated instrument having a distal end and including a distal electrode configured for ablation and a proximal electrode electrically insulated from the distal electrode;
- an electrical generator configured to apply electrical energy to the distal electrode; and
- an impedance monitoring module configured to:
  - measure a first distal impedance at the distal electrode to detect a first distal decrease indicative of the distal electrode being in contact with blood;
  - measure a second distal impedance at the distal electrode to detect a first distal increase indicative of the distal electrode being in contact with tissue;
  - measure a third distal impedance at the distal electrode when the application of electrical energy by the electrical generator begins;
  - measure a first proximal impedance at the proximal electrode to detect a first proximal increase indicative of the proximal electrode being in contact with tissue; and
  - after detecting the first proximal increase, measure a second proximal impedance at the proximal electrode to detect a first proximal decrease indicative of the proximal electrode being in contact with blood,
- the electrical generator configured to suspend electrical energy to the distal electrode upon detection of the first proximal decrease.

2. The system of claim 1, wherein the guiding instrument includes a guiding sheath.

3. The system of claim 1, wherein the elongated instrument includes a needle instrument.

4. The system of claim 1, wherein the distal electrode is atraumatic, being devoid of a tissue-piercing distal end.

5. The system of claim 1, wherein the distal electrode is configured as a monopolar electrode for tissue ablation.

6. The system of claim 1, wherein the distal electrode is configured as a bipolar electrode for tissue ablation.

7. The system of claim 1, wherein the distal electrode and the proximal electrode are separated on the elongated instrument by a predetermined distance.

8. The system of claim 1, further including a return pad configured to be affixed to a patient's body to enable the impedance monitoring module to measure the impedance at the proximal electrode.

9. The system of claim 8, wherein electrical energy applied to the proximal electrode generates a current that is distributed through the patient's body to the return pad.

10. A method of transseptal puncture, comprising:
- positioning a guiding instrument near a septum with an atraumatic needle instrument slidably disposed in a lumen of the guiding instrument, the atraumatic needle instrument including a distal electrode and a proximal electrode;
- deploying the atraumatic needle instrument from the lumen with distal advancement relative to the guiding instrument;
- measuring a first distal impedance at the distal electrode to detect a first distal decrease indicative of the distal electrode being in contact with blood;
- measuring a second distal impedance at the distal electrode to detect a first distal increase indicative of the distal electrode being in contact with the septum;
- energizing the distal electrode to ablate the septum;
- measuring a third distal impedance at the distal electrode when the energization of the distal electrode begins;
- measuring a first proximal impedance at the proximal electrode to detect a first proximal increase indicative of the proximal electrode being in contact with the septum;
- after detecting the first proximal increase, measuring a second proximal impedance at the proximal electrode to detect a first proximal decrease indicative of the proximal electrode being in contact with blood; and
- suspending energization of the distal electrode upon detection of the first proximal decrease.

11. The method of claim 10, further comprising suspending distal advancement of the atraumatic needle instrument upon detection of the first proximal decrease.

12. The method of claim 10, wherein the proximal electrode is a nonablation electrode.

13. A method of transseptal puncture, comprising:
- positioning a guiding instrument near a septum with an atraumatic needle instrument slidably disposed in a lumen of the guiding instrument, the atraumatic needle instrument including a distal electrode and a proximal electrode;
- providing a predetermined threshold impedance;
- deploying the atraumatic needle instrument from the lumen with distal advancement relative to the guiding instrument;
- measuring a first distal impedance at the distal electrode to detect a first distal decrease relative to the predetermined threshold impedance indicative of the distal electrode being in contact with blood;
- measuring a second distal impedance at the distal electrode to detect a first distal increase relative to the predetermined threshold impedance indicative of the distal electrode being in contact with the septum;
- energizing the distal electrode to ablate the septum;
- measuring a third distal impedance at the distal electrode when the energization of the distal electrode begins and comparing the third distal impedance to the predetermined threshold impedance;

measuring a first proximal impedance at the proximal electrode to detect a first proximal increase relative to the predetermined threshold impedance indicative of the proximal electrode being in contact with the septum;

after detecting the first proximal increase, measuring a second proximal impedance at the proximal electrode to detect a first proximal decrease relative to the predetermined threshold impedance indicative of the proximal electrode being in contact with blood; and suspending energization of the distal electrode upon detection of the first proximal decrease.

* * * * *